(12) United States Patent
Suzumura et al.

(10) Patent No.: US 7,037,698 B2
(45) Date of Patent: May 2, 2006

(54) PYRROLOQUINOLINE QUINONE-DEPENDENT GLUCOSE DEHYDROGENASE

(75) Inventors: Akitoshi Suzumura, Kakamigahara (JP); Norio Hamamatsu, Tsukuba (JP)

(73) Assignee: Amano Enzyme Inc., Nagoya (JP)

( * ) Notice: Subject to any disclaimer, the term of this patent is extended or adjusted under 35 U.S.C. 154(b) by 0 days.

(21) Appl. No.: 10/847,867

(22) Filed: May 19, 2004

(65) Prior Publication Data

US 2005/0260728 A1 Nov. 24, 2005

(51) Int. Cl.
*C12N 9/04* (2006.01)
*C12N 15/53* (2006.01)
*C12N 1/15* (2006.01)
*C12N 1/19* (2006.01)
*C12N 1/21* (2006.01)

(52) U.S. Cl. ............... 435/190; 435/189; 435/69.1; 435/320.1; 435/252.3; 536/23.2

(58) Field of Classification Search ............ 435/190, 435/189, 69.1, 320.1, 252.3
See application file for complete search history.

(56) References Cited

U.S. PATENT DOCUMENTS

| 2003/0104595 A1* | 6/2003 | Kratzch et al. ............ 435/189 |
| 2003/0232418 A1* | 12/2003 | Takeshima et al. ......... 435/189 |
| 2004/0005683 A1 | 1/2004 | Kratzsch et al. |

FOREIGN PATENT DOCUMENTS

| EP | 1367120 A2 | 12/2003 |
| JP | 03-133382 | 6/1991 |
| JP | 03-502881 | 7/1991 |
| JP | 05-328974 | 12/1993 |
| JP | 2000-312588 | 11/2000 |
| JP | 2000-350588 | 12/2000 |
| JP | 2001-197888 | 7/2001 |
| JP | 2001-346587 | 12/2001 |
| JP | 2004-173538 | 6/2004 |
| WO | WO 02/34919 A1 | 5/2002 |

OTHER PUBLICATIONS

A.M.-Cleton-Jansen, et al.; Cloning, characterization and DNA sequencing of the gene encoding the $M_r50\,000$ quinoprotein glucose dehydrogenase from *Acinetobacter calcoaceticus*; Mol Gen Genet; vol. 217; 1989, pp. 430-436./Discussed in the specification.
European Search Report mailed Oct. 6, 2004.

* cited by examiner

*Primary Examiner*—Rebecca E. Prouty
*Assistant Examiner*—Kagnew Gebreyesus

(74) *Attorney, Agent, or Firm*—Armstrong, Kratz, Quintos, Hanson & Brooks, LLP

(57) ABSTRACT

A modified pyrroloquinoline quinone-dependent glucose dehydrogenase having a low reactivity with respect to maltose, galactose, etc. is provided. A modified pyrroloquinoline quinone-dependent glucose dehydrogenase including an amino acid sequence in which one or more amino acids in a region corresponding to a first region consisting of amino acids at positions 326 to 354 in pyrroloquinoline quinone-dependent glucose dehydrogenase derived from *Acinetobacter calcoaceticus* are substituted as compared with an amino acid sequence of the corresponding wild-type enzyme.

5 Claims, 6 Drawing Sheets

Fig.1

Asp Val Pro Leu Thr Pro Ser Gln Phe Ala Lys Ala Lys Thr Glu Ser Phe Asp Lys
Lys Val Leu Leu Ser Asn Leu Asn Lys Pro His Ala Leu Leu Trp Gly Pro Asp Asn Gln Ile Trp
Leu Thr Glu Arg Ala Thr Gly Lys Ile Leu Arg Val Asn Pro Glu Ser Gly Ser Val Lys Thr Val
Phe Gln Val Pro Glu Ile Val Asn Asp Ala Asp Gly Gln Asn Gly Leu Leu Gly Phe Ala Phe His
Pro Asp Phe Lys Asn Asn Pro Tyr Ile Tyr Val Ser Gly Thr Phe Lys Asn Pro Lys Ser Thr Asp
Lys Glu Leu Pro Asn Gln Thr Ile Ile Arg Arg Tyr Thr Tyr Asn Lys Ala Thr Asp Thr Leu Glu
Lys Pro Val Asp Leu Leu Ala Gly Leu Pro Ser Ser Lys Asp His Gln Ser Gly Arg Leu Val Ile
Gly Pro Asp Gln Lys Ile Tyr Tyr Thr Ile Gly Asp Gln Gly Arg Asn Gln Leu Ala Tyr Leu Phe
Leu Pro Asn Gln Ala Gln His Thr Pro Thr Gln Gln Glu Leu Ser Gly Lys Asp Tyr His Thr Tyr
Met Gly Lys Val Leu Arg Leu Asn Leu Asp Gly Ser Ile Pro Lys Asp Asn Pro Ser Phe Asn Gly
Val Ile Ser His Ile Tyr Thr Leu Gly His Arg Asn Pro Gln Gly Leu Ala Phe Thr Pro Asn Gly
Lys Leu Leu Gln Ser Glu Gln Gly Pro Asn Ser Asp Asp Glu Ile Asn Leu Ile Val Lys Gly Gly
Asn Tyr Gly Trp Pro Asn Val Ala Gly Tyr Lys Asp Asp Ser Gly Tyr Ala Tyr Ala Asn Tyr Ser
Ala Ala Ser Asn Lys Ala Gln Ile Lys Asp Leu Gly Gln Asn Gly Leu Lys Val Ala Ala Gly Val
Pro Val Thr Lys Glu Ser Glu Trp Thr Gly Lys Asn Phe Val Pro Pro Leu Lys Thr Leu Tyr Thr
Val Gln Asp Thr Tyr Asn Tyr Asn Asp Pro Thr Cys Gly Asp Met Thr Tyr Ile Cys Trp Pro Thr
Val Ala Pro Ser Ser Ala Tyr Val Tyr Lys Gly Gly Lys Lys Ala Ile Ser Gly Trp Glu Asn Thr
Leu Leu Val Pro Ser Leu Lys Arg Gly Val Ile Phe Arg Ile Lys Leu Asp Pro Thr Tyr Ser Ala
Thr Tyr Asp Asp Ala Val Pro Met Phe Lys Ser Asn Asn Arg Tyr Arg Asp Val Ile Ala Ser Pro
Asp Gly Asn Val Leu Tyr Val Leu Thr Asp Thr Ser Gly Asn Val Gln Lys Asp Asp Gly Ser Val
Thr Asn Thr Leu Glu Asn Pro Gly Ser Leu Ile Lys Phe Thr Tyr Lys Ala Lys ***

```
GAT GTT CCT CTT ACA CCA TCT CAA TTT GCT AAA GCG AAA ACA GAA AGC TTT GAC
AAG AAA GTT CTTCTATCTAATTTAAATAAGCCACATGCTTTGTTGTGGGGGCCTGATAATCAAATTT
GGTTAACGGAGCGGGCAACAGGGAAGATTCTAAGAGTGAATCCAGAGTCGGGCAGTGTAAAAACAG
TTTTTCAGGTTCCTGAGATTGTAAATGATGCTGATGGACAAAACGGTTTATTGGGTTTTGCCTTTCATC
CTGACTTTAAAAATAATCCTTATATCTATGTTTCAGGTACTTTTAAAAATCCGAAATCTACAGATAAAGA
ATTACCGAATCAAACTATTATTCGTCGATATACCTATAACAAAGCAACAGATACTCTTGAGAAACCAGT
AGATTTATTAGCAGGATTACCTTCATCGAAAGACCATCAGTCGGGTCGCCTTGTCATTGGTCCAGACCA
AAAGATTTACTATACGATTGGTGATCAGGGGCGTAACCAGCTGGCTTATTTATTCTTACCAAATCAAGC
ACAGCATACGCCGACTCAACAGGAACTGAGCGGCAAAGACTATCATACCTATATGGGTAAAGTATTAC
GCTTAAATCTGGATGGAAGTATTCCAAAAGATAATCCAAGCTTTAACGGTGTAATTAGCCATATTTATAC
GCTCGGTCATCGTAATCCACAGGGCTTGGCATTTACTCCAAATGGTAAACTGTTGCAATCTGAACAGG
GTCCAAACTCTGACGATGAAATTAACCTCATTGTCAAAGGTGGTAACTATGGCTGGCCAAATGTAGCG
GGTTATAAAGATGATAGTGGTTATGCCTATGCAAATTATTCGGCAGCAAGCAATAAAGCACAAATTAAA
GATTTAGGACAAAATGGTTTAAAAGTGGCAGCTGGCGTTCCAGTGACTAAAGAGTCTGAATGGACTG
GTAAAAACTTTGTACCGCCGTTAAAAACTTTATATACCGTCCAAGATACCTATAACTATAATGACCCAA
CCTGTGGGGATATGACCTACATTTGCTGGCCAACGGTTGCGCCGTCATCTGCTTATGTCTATAAGGGAG
GCAAAAAAGCAATTTCTGGTTGGGAAAATACCTTATTGGTTCCATCTTTAAAGCGCGGTGTTATTTTCC
GTATTAAGCTAGATCCAACTTACAGTGCTACTTATGATGATGCTGTGCCGATGTTTAAGAGCAACAATC
GTTATCGTGACGTGATTGCAAGTCCAGATGGAAATGTTTTATATGTATTGACTGATACTTCCGGAAATGT
CCAAAAAGATGATGGTTCTGTAACGAATACATTAGAAAACCCAGGATCTCTCATTAAGTTCACCTATAA
GGCTAAGTAA
```

Fig.2

Met Asn Lys His Leu Leu Ala Lys Ile Thr Leu Leu Gly Ala Ala Gln Leu Leu Thr Leu Asn Ser
Ala Phe Ala Asp Val Pro Leu Thr Pro Ser Gln Phe Ala Lys Ala Lys Thr Glu Ser Phe Asp Lys
Lys Val Leu Leu Ser Asn Leu Asn Lys Pro His Ala Leu Leu Trp Gly Pro Asp Asn Gln Ile Trp
Leu Thr Glu Arg Ala Thr Gly Lys Ile Leu Arg Val Asn Pro Glu Ser Gly Ser Val Lys Thr Val
Phe Gln Val Pro Glu Ile Val Asn Asp Ala Asp Gly Gln Asn Gly Leu Leu Gly Phe Ala Phe His
Pro Asp Phe Lys Asn Asn Pro Tyr Ile Tyr Val Ser Gly Thr Phe Lys Asn Pro Lys Ser Thr Asp
Lys Glu Leu Pro Asn Gln Thr Ile Ile Arg Arg Tyr Thr Tyr Asn Lys Ala Thr Asp Thr Leu Glu
Lys Pro Val Asp Leu Leu Ala Gly Leu Pro Ser Ser Lys Asp His Gln Ser Gly Arg Leu Val Ile
Gly Pro Asp Gln Lys Ile Tyr Tyr Thr Ile Gly Asp Gln Gly Arg Asn Gln Leu Ala Tyr Leu Phe
Leu Pro Asn Gln Ala Gln His Thr Pro Thr Gln Gln Glu Leu Ser Gly Lys Asp Tyr His Thr Tyr
Met Gly Lys Val Leu Arg Leu Asn Leu Asp Gly Ser Ile Pro Lys Asp Asn Pro Ser Phe Asn Gly
Val Ile Ser His Ile Tyr Thr Leu Gly His Arg Asn Pro Gln Gly Leu Ala Phe Thr Pro Asn Gly
Lys Leu Leu Gln Ser Glu Gln Gly Pro Asn Ser Asp Asp Glu Ile Asn Leu Ile Val Lys Gly Gly
Asn Tyr Gly Trp Pro Asn Val Ala Gly Tyr Lys Asp Asp Ser Gly Tyr Ala Tyr Ala Asn Tyr Ser
Ala Ala Ser Asn Lys Ala Gln Ile Lys Asp Leu Gly Gln Asn Gly Leu Lys Val Ala Ala Gly Val
Pro Val Thr Lys Glu Ser Glu Trp Thr Gly Lys Asn Phe Val Pro Pro Leu Lys Thr Leu Tyr Thr
Val Gln Asp Thr Tyr Asn Tyr Asn Asp Pro Thr Cys Gly Asp Met Thr Tyr Ile Cys Trp Pro Thr
Val Ala Pro Ser Ser Ala Tyr Val Tyr Lys Gly Gly Lys Lys Ala Ile Ser Gly Trp Glu Asn Thr
Leu Leu Val Pro Ser Leu Lys Arg Gly Val Ile Phe Arg Ile Lys Leu Asp Pro Thr Tyr Ser Ala
Thr Tyr Asp Asp Ala Val Pro Met Phe Lys Ser Asn Asn Arg Tyr Arg Asp Val Ile Ala Ser Pro
Asp Gly Asn Val Leu Tyr Val Leu Thr Asp Thr Ser Gly Asn Val Gln Lys Asp Asp Gly Ser Val
Thr Asn Thr Leu Glu Asn Pro Gly Ser Leu Ile Lys Phe Thr Tyr Lys Ala Lys ***

ATGAATAAACATTTATTGGCTAAAATTACTTTATTAGGCGCTGCTCAGCTACTTACGCTCAATTCAGCAT
TTGCTGATGTTCCTCTTACACCATCTCAATTTGCTAAAGCGAAAACAGAAAGCTTTGACAAGAAAGTT
CTTCTATCTAATTTAAATAAGCCACATGCTTTGTTGTGGGGGCCTGATAATCAAATTTGGTTAACGGAG
CGGGCAACAGGGAAGATTCTAAGAGTGAATCCAGAGTCGGGCAGTGTAAAAACAGTTTTTCAGGTTC
CTGAGATTGTAAATGATGCTGATGGACAAAACGGTTTATTGGGTTTTGCCTTTCATCCTGACTTTAAAA
ATAATCCTTATATCTATGTTTCAGGTACTTTTTAAAAATCCGAAATCTACAGATAAAGAATTACCGAATCA
AACTATTATTCGTCGATATACCTATAACAAAGCAACAGATACTCTTGAGAAACCAGTAGATTTATTAGC
AGGATTACCTTCATCGAAAGACCATCAGTCGGGTCGCCTTGTCATTGGTCCAGACCAAAAGATTTACT
ATACGATTGGTGATCAGGGGCGTAACCAGCTGGCTTATTTATTCTTACCAAATCAAGCACAGCATACGC
CGACTCAACAGGAACTGAGCGGCAAAGACTATCATACCTATATGGGTAAAGTATTACGCTTAAATCTG
GATGGAAGTATTCCAAAAGATAATCCAAGCTTTAACGGTGTAATTAGCCATATTTATACGCTCGGTCATC
GTAATCCACAGGGCTTGGCATTTACTCCAAATGGTAAACTGTTGCAATCTGAACAGGGTCCAAACTCT
GACGATGAAATTAACCTCATTGTCAAAGGTGGTAACTATGGCTGGCCAAATGTAGCGGGTTATAAAGA
TGATAGTGGTTATGCCTATGCAAATTATTCGGCAGCAAGCAATAAAGCACAAATTAAAGATTTAGGACA
AAATGGTTTAAAAGTGGCAGCTGGCGTTCCAGTGACTAAAGAGTCTGAATGGACTGGTAAAAACTTT
GTACCGCCGTTAAAAACTTTATATACCGTCCAAGATACCTATAACTATAATGACCCAACCTGTGGGGATA
TGACCTACATTTGCTGGCCAACGGTTGCGCCGTCATCTGCTTATGTCTATAAGGGAGGCAAAAAAGCA
ATTTCTGGTTGGGAAAATACCTTATTGGTTCCATCTTTAAAGCGCGGTGTTATTTTCCGTATTAAGCTAG
ATCCAACTTACAGTGCTACTTATGATGATGCTGTGCCGATGTTTAAGAGCAACAATCGTTATCGTGACG
TGATTGCAAGTCCAGATGGAAATGTTTTATATGTATTGACTGATACTTCCGGAAATGTCCAAAAAGATG
ATGGTTCTGTAACGAATACATTAGAAAACCCAGGATCTCTCATTAAGTTCACCTATAAGGCTAAGTAA

Fig.4

| name of primer | sequence | length |
|---|---|---|
| SEQ ID NO : 9 | : 5'-TCACATGTTCTTTCCTGCGTTATC-3' | (24mer) |
| S-Primer(G)-9-QL | : 5'-gATCAggggCgTAACCAACTggCTTATTTATTCTT-3' | (35mer) |
| S-Primer(G)-9-GL | : 5'-gATCAggggCgTAACggTCTggCTTATTTATTCTT-3' | (35mer) |
| S-Primer(G)-9-SL | : 5'-gATCAggggCgTAACAgCCTggCTTATTTATTCTT-3' | (35mer) |
| S-Primer(G)-9-YL | : 5'-gATCAggggCgTAACTATCTggCTTATTTATTCTT-3' | (35mer) |
| S-Primer(G)-9-QF | : 5'-gATCAggggCgTAACCAgTTTgCTTATTTATTCTT-3' | (35mer) |
| S-Primer(G)-9-GF | : 5'-gATCAggggCgTAACggTTTTgCTTATTTATTCTT-3' | (35mer) |
| S-Primer(G)-9-SF | : 5'-gATCAggggCgTAACAgCTTTgCTTATTTATTCTT-3' | (35mer) |
| S-Primer(G)-9-YF | : 5'-gATCAggggCgTAACTATTTTgCTTATTTATTCTT-3' | (35mer) |
| SEQ ID NO : 27 | : 5'-AAgAATAAATAAgCCAgTTggTTACgCCCCTgATC-3' | (35mer) |
| S-Primer(G)-10-GL | : 5'-AAgAATAAATAAgCCAgACCgTTACgCCCCTgATC-3' | (35mer) |
| S-Primer(G)-10-SL | : 5'-AAgAATAAATAAgCCAggCTgTTACgCCCCTgATC-3' | (35mer) |
| S-Primer(G)-10-YL | : 5'-AAgAATAAATAAgCCAgATAgTTACgCCCCTgATC-3' | (35mer) |
| S-Primer(G)-10-QF | : 5'-AAgAATAAATAAgCAAACTggTTACgCCCCTgATC-3' | (35mer) |
| S-Primer(G)-10-GF | : 5'-AAgAATAAATAAgCAAAACCgTTACgCCCCTgATC-3' | (35mer) |
| S-Primer(G)-10-SF | : 5'-AAgAATAAATAAgCAAAgCTgTTACgCCCCTgATC-3' | (35mer) |
| S-Primer(G)-10-YF | : 5'-AAgAATAAATAAgCAAAATAgTTACgCCCCTgATC-3' | (35mer) |
| S-primer(G)-4 | : 5'-TGGCGTTCCAGTGACTAAAG-3' | (20mer) |
| S-primer(G)-11 | : 5'-ACAAAgTTTTTACCAgTCCA-3' | (20mer) |
| S-primer(G)-12-W | : 5'-ACCTACATTTgCTggCCGACggTT-3' | (24mer) |
| S-primer(G)-12-H | : 5'-ACCTACATTTgCCATCCAACggTT-3' | (24mer) |
| S-primer(G)-13-W | : 5'-AACCgTCggCCAgCAAATgTAggT-3' | (24mer) |
| S-primer(G)-13-H | : 5'-AACCgTTggATggCAAATgTAggT-3' | (24mer) |
| S-primer(G)-14 | : 5'-TTTAAAgCgCggTgTTATTT-3' | (20mer) |
| S-primer(G)-5 | : 5'-TGCAATCACGTCACGATAAC-3' | (20mer) |
| S-primer(G)-15 | : 5'-TCCggAAATgTCCAAAAAgATgATggTTCT-3' | (30mer) |
| SEQ ID NO : 12 | : 5'-ggCgCgTACTATggTTgCTTTgAC-3' | (24mer) |

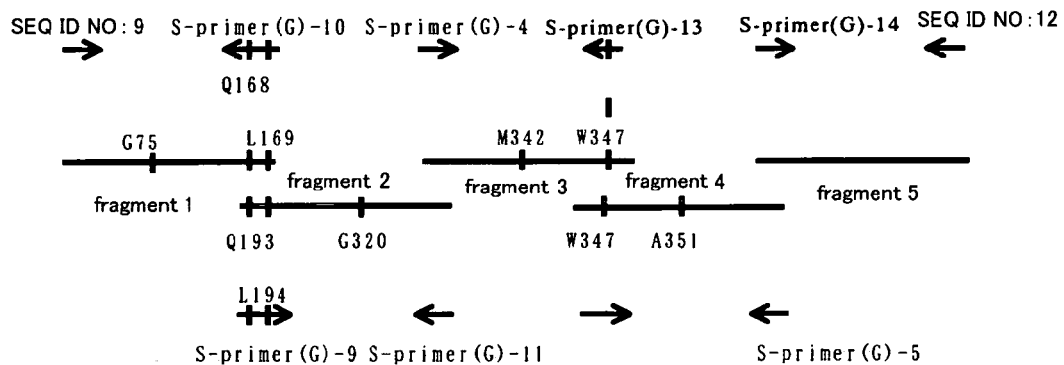

Fig.5

| template | fragment | | mixing ratio | |
|---|---|---|---|---|
| | forward primer | reverse primer | | |
| | S-primer (G)- | S-primer (G)- | | |
| fragment 1 (wild type) | SEQ ID NO:9 | 10-YF | 0.2*(0.5/3)*0.5= | 0.017 |
| | | 10-SF | 0.2*(0.5/3)*0.5= | 0.017 |
| | | 10-GF | 0.2*(0.5/3)*0.5= | 0.017 |
| | | 10-QF | 0.2*0.5*0.5= | 0.050 |
| | | 10-YL | 0.2*(0.5/3)*0.5= | 0.017 |
| | | 10-SL | 0.2*(0.5/3)*0.5= | 0.017 |
| | | 10-GL | 0.2*(0.5/3)*0.5= | 0.017 |
| | | 10-QL | 0.2*0.5*0.5= | 0.050 |
| fragment 1 (G 75 mutant) | SEQ ID NO:9 | 10-YF | 0.8*(0.5/3)*0.5= | 0.067 |
| | | 10-SF | 0.8*(0.5/3)*0.5= | 0.067 |
| | | 10-GF | 0.8*(0.5/3)*0.5= | 0.067 |
| | | 10-QF | 0.8*0.5*0.5= | 0.200 |
| | | 10-YL | 0.8*(0.5/3)*0.5= | 0.067 |
| | | 10-SL | 0.8*(0.5/3)*0.5= | 0.067 |
| | | 10-GL | 0.8*(0.5/3)*0.5= | 0.067 |
| | | 10-QL | 0.8*0.5*0.5= | 0.200 |
| fragment 2 (wild type) | 9-YF | 11 | 0.2*(0.5/3)*0.5= | 0.017 |
| | 9-SF | | 0.2*(0.5/3)*0.5= | 0.017 |
| | 9-GF | | 0.2*(0.5/3)*0.5= | 0.017 |
| | 9-QF | | 0.2*0.5*0.5= | 0.050 |
| | 9-YL | | 0.2*(0.5/3)*0.5= | 0.017 |
| | 9-SL | | 0.2*(0.5/3)*0.5= | 0.017 |
| | 9-GL | | 0.2*(0.5/3)*0.5= | 0.017 |
| | 9-QL | | 0.2*0.5*0.5= | 0.050 |
| fragment 2 (G 295 mutant mixture) | 9-YF | 11 | 0.8*(0.5/3)*0.5= | 0.067 |
| | 9-SF | | 0.8*(0.5/3)*0.5= | 0.067 |
| | 9-GF | | 0.8*(0.5/3)*0.5= | 0.067 |
| | 9-QF | | 0.8*0.5*0.5= | 0.200 |
| | 9-YL | | 0.8*(0.5/3)*0.5= | 0.067 |
| | 9-SL | | 0.8*(0.5/3)*0.5= | 0.067 |
| | 9-GL | | 0.8*(0.5/3)*0.5= | 0.067 |
| | 9-QL | | 0.8*0.5*0.5= | 0.200 |
| fragment 3 (wild type) | 4 | 13-H | 0.2*0.5= | 0.1 |
| | | 13-W | 0.2*0.5= | 0.1 |
| fragment 3 (M342 P mutant) | 4 | 13-H | 0.8*0.5= | 0.4 |
| | | 13-W | 0.8*0.5= | 0.4 |
| fragment 4 (wild type) | 12-H | 5 | 0.2*0.5= | 0.1 |
| | 12-W | | 0.2*0.5= | 0.1 |
| fragment 4 (A 351T mutant) | 12-H | 5 | 0.8*0.5= | 0.4 |
| | 12-W | | 0.8*0.5= | 0.4 |
| fragment 5 (wild type) | 14 | SEQ ID NO:10 | | 1 |

Fig.6

| | G75 | Q168 | L169 | G295 | M342 | W347 | A351 | glucose | maltose | lactose | galactose |
|---|---|---|---|---|---|---|---|---|---|---|---|
| wild type | Gly | Gln | Leu | Gly | Met | Trp | Ala | 100 | 90 | 75 | 34 |
| No. 1 | | | Phe | Glu | Pro | | Thr | 100 | 10 | 39 | 4 |
| No. 2 | | | | Asp | | | Thr | 100 | 22 | 48 | 13 |
| No. 3 | | | | Tyr | Pro | | Thr | 100 | 45 | 79 | 29 |
| No. 4 | | | | Phe | Pro | | Thr | 100 | 43 | 77 | 23 |
| No. 5 | | | Phe | Glu | Pro | | | 100 | 44 | 72 | 40 |
| No. 6 | Trp | | | Glu | Pro | | Thr | 100 | 38 | 62 | 9 |
| No. 7 | | | | | Pro | | Thr | 100 | 17 | 34 | 0 |

SEQUENCE LISTING

```
<160> NUMBER OF SEQ ID NOS: 34

<210> SEQ ID NO 1
<211> LENGTH: 455
<212> TYPE: PRT
<213> ORGANISM: Acinetobacter calcoaceticus

<400> SEQUENCE: 1

Asp Val Pro Leu Thr Pro Ser Gln Phe Ala Lys Ala Lys Thr Glu Ser
1               5                   10                  15

Phe Asp Lys Lys Val Leu Leu Ser Asn Leu Asn Lys Pro His Ala Leu
            20                  25                  30

Leu Trp Gly Pro Asp Asn Gln Ile Trp Leu Thr Glu Arg Ala Thr Gly
        35                  40                  45

Lys Ile Leu Arg Val Asn Pro Glu Ser Gly Ser Val Lys Thr Val Phe
    50                  55                  60

Gln Val Pro Glu Ile Val Asn Asp Ala Asp Gly Gln Asn Gly Leu Leu
65                  70                  75                  80

Gly Phe Ala Phe His Pro Asp Phe Lys Asn Asn Pro Tyr Ile Tyr Val
            85                  90                  95

Ser Gly Thr Phe Lys Asn Pro Lys Ser Thr Asp Lys Glu Leu Pro Asn
            100                 105                 110

Gln Thr Ile Ile Arg Arg Tyr Thr Tyr Asn Lys Ala Thr Asp Thr Leu
            115                 120                 125

Glu Lys Pro Val Asp Leu Leu Ala Gly Leu Pro Ser Ser Lys Asp His
    130                 135                 140

Gln Ser Gly Arg Leu Val Ile Gly Pro Asp Gln Lys Ile Tyr Tyr Thr
145                 150                 155                 160

Ile Gly Asp Gln Gly Arg Asn Gln Leu Ala Tyr Leu Phe Leu Pro Asn
            165                 170                 175

Gln Ala Gln His Thr Pro Thr Gln Gln Glu Leu Ser Gly Lys Asp Tyr
            180                 185                 190

His Thr Tyr Met Gly Lys Val Leu Arg Leu Asn Leu Asp Gly Ser Ile
            195                 200                 205

Pro Lys Asp Asn Pro Ser Phe Asn Gly Val Ile Ser His Ile Tyr Thr
    210                 215                 220

Leu Gly His Arg Asn Pro Gln Gly Leu Ala Phe Thr Pro Asn Gly Lys
225                 230                 235                 240
```

-continued

| | | | | | | | | | | | |
|---|---|---|---|---|---|---|---|---|---|---|---|
| Leu | Leu | Gln | Ser | Glu | Gln | Gly | Pro | Asn | Ser | Asp | Asp Glu Ile Asn Leu |
| | | | 245 | | | | | 250 | | | 255 |
| Ile | Val | Lys | Gly | Gly | Asn | Tyr | Gly | Trp | Pro | Asn | Val Ala Gly Tyr Lys |
| | | | 260 | | | | | 265 | | | 270 |
| Asp | Asp | Ser | Gly | Tyr | Ala | Tyr | Ala | Asn | Tyr | Ser | Ala Ala Ser Asn Lys |
| | | | 275 | | | | | 280 | | | 285 |
| Ala | Gln | Ile | Lys | Asp | Leu | Gly | Gln | Asn | Gly | Leu | Lys Val Ala Ala Gly |
| | | | 290 | | | | | 295 | | | 300 |
| Val | Pro | Val | Thr | Lys | Glu | Ser | Glu | Trp | Thr | Gly | Lys Asn Phe Val Pro |
| 305 | | | | 310 | | | | | 315 | | 320 |
| Pro | Leu | Lys | Thr | Leu | Tyr | Thr | Val | Gln | Asp | Thr | Tyr Asn Tyr Asn Asp |
| | | | | 325 | | | | | 330 | | 335 |
| Pro | Thr | Cys | Gly | Asp | Met | Thr | Tyr | Ile | Cys | Trp | Pro Thr Val Ala Pro |
| | | | 340 | | | | | 345 | | | 350 |
| Ser | Ser | Ala | Tyr | Val | Tyr | Lys | Gly | Gly | Lys | Lys | Ala Ile Ser Gly Trp |
| | | | | 355 | | | | | 360 | | 365 |
| Glu | Asn | Thr | Leu | Leu | Val | Pro | Ser | Leu | Lys | Arg | Gly Val Ile Phe Arg |
| | 370 | | | | | 375 | | | | | 380 |
| Ile | Lys | Leu | Asp | Pro | Thr | Tyr | Ser | Ala | Thr | Tyr | Asp Asp Ala Val Pro |
| 385 | | | | | 390 | | | | | 395 | 400 |
| Met | Phe | Lys | Ser | Asn | Asn | Arg | Tyr | Arg | Asp | Val | Ile Ala Ser Pro Asp |
| | | | | 405 | | | | | 410 | | 415 |
| Gly | Asn | Val | Leu | Tyr | Val | Leu | Thr | Asp | Thr | Ser | Gly Asn Val Gln Lys |
| | | | | 420 | | | | | 425 | | 430 |
| Asp | Asp | Gly | Ser | Val | Thr | Asn | Thr | Leu | Glu | Asn | Pro Gly Ser Leu Ile |
| | | | 435 | | | | | 440 | | | 445 |
| Lys | Phe | Thr | Tyr | Lys | Ala | Lys | | | | | |
| | | | 450 | | | 455 | | | | | |

<210> SEQ ID NO 2
<211> LENGTH: 1368
<212> TYPE: DNA
<213> ORGANISM: Acinetobacter calcoaceticus

<400> SEQUENCE: 2

| | |
|---|---|
| gatgttcctc ttacaccatc tcaatttgct aaagcgaaaa cagaaagctt tgacaagaaa | 60 |
| gttcttctat ctaatttaaa taagccacat gctttgttgt gggggcctga taatcaaatt | 120 |
| tggttaacgg agcgggcaac agggaagatt ctaagagtga atccagagtc gggcagtgta | 180 |
| aaaacagttt ttcaggttcc tgagattgta atgatgctg atggacaaaa cggtttattg | 240 |
| ggttttgcct ttcatcctga cttaaaaat aatccttata tctatgtttc aggtactttt | 300 |
| aaaaatccga atctacaga taagaatta ccgaatcaaa ctattattcg tcgatatacc | 360 |
| tataacaaag caacagatac tcttgagaaa ccagtagatt tattagcagg attaccttca | 420 |
| tcgaaagacc atcagtcggg tcgccttgtc attggtccag accaaaagat ttactatacg | 480 |
| attggtgatc agggcgtaa ccagctggct tatttattct taccaaatca agcacagcat | 540 |
| acgccgactc aacaggaact gagcggcaaa gactatcata cctatatggg taaagtatta | 600 |
| cgcttaaatc tggatggaag tattccaaaa gataatccaa gctttaacgg tgtaattagc | 660 |
| catatttata cgctcggtca tcgtaatcca cagggcttgg catttactcc aaatggtaaa | 720 |
| ctgttgcaat ctgaacaggg tccaaactct gacgatgaaa ttaacctcat tgtcaaaggt | 780 |
| ggtaactatg gctggccaaa tgtagcgggt tataaagatg atagtggtta tgcctatgca | 840 |
| aattattcgg cagcaagcaa taagcacaa attaaagatt taggacaaaa tggtttaaaa | 900 |

```
gtggcagctg cgttccagt  gactaaagag tctgaatgga ctggtaaaaa ctttgtaccg    960
ccgttaaaaa ctttatatac cgtccaagat acctataact ataatgaccc aacctgtggg   1020
gatatgacct acatttgctg ccaacggtt  gcgccgtcat ctgcttatgt ctataaggga   1080
ggcaaaaaag caatttctgg ttgggaaaat accttattgg ttccatcttt aaagcgcggt   1140
gttatttttcc gtattaagct agatccaact tacagtgcta cttatgatga tgctgtgccg   1200
atgtttaaga gcaacaatcg ttatcgtgac gtgattgcaa gtccagatgg aaatgtttta   1260
tatgtattga ctgatacttc cggaaatgtc caaaaagatg atggttctgt aacgaataca   1320
ttagaaaacc caggatctct cattaagttc acctataagg ctaagtaa              1368
```

<210> SEQ ID NO 3
<211> LENGTH: 480
<212> TYPE: PRT
<213> ORGANISM: Acinetobacter calcoaceticus

<400> SEQUENCE: 3

```
Met Asn Lys His Leu Leu Ala Lys Ile Thr Leu Leu Gly Ala Ala Gln
1               5                   10                  15

Leu Leu Thr Leu Asn Ser Ala Phe Ala Asp Val Pro Leu Thr Pro Ser
                20                  25                  30

Gln Phe Ala Lys Ala Lys Thr Glu Ser Phe Asp Lys Lys Val Leu Leu
            35                  40                  45

Ser Asn Leu Asn Lys Pro His Ala Leu Leu Trp Gly Pro Asp Asn Gln
        50                  55                  60

Ile Trp Leu Thr Glu Arg Ala Thr Gly Lys Ile Leu Arg Val Asn Pro
65                  70                  75                  80

Glu Ser Gly Ser Val Lys Thr Val Phe Gln Val Pro Glu Ile Val Asn
                85                  90                  95

Asp Ala Asp Gly Gln Asn Gly Leu Leu Gly Phe Ala Phe His Pro Asp
            100                 105                 110

Phe Lys Asn Asn Pro Tyr Ile Tyr Val Ser Gly Thr Phe Lys Asn Pro
        115                 120                 125

Lys Ser Thr Asp Lys Glu Leu Pro Asn Gln Thr Ile Ile Arg Arg Tyr
130                 135                 140

Thr Tyr Asn Lys Ala Thr Asp Thr Leu Glu Lys Pro Val Asp Leu Leu
145                 150                 155                 160

Ala Gly Leu Pro Ser Ser Lys Asp His Gln Ser Gly Arg Leu Val Ile
                165                 170                 175

Gly Pro Asp Gln Lys Ile Tyr Tyr Thr Ile Gly Asp Gln Gly Arg Asn
            180                 185                 190

Gln Leu Ala Tyr Leu Phe Leu Pro Asn Gln Ala Gln His Thr Pro Thr
        195                 200                 205

Gln Gln Glu Leu Ser Gly Lys Asp Tyr His Thr Tyr Met Gly Lys Val
    210                 215                 220

Leu Arg Leu Asn Leu Asp Gly Ser Ile Pro Lys Asp Asn Pro Ser Phe
225                 230                 235                 240

Asn Gly Val Ile Ser His Ile Tyr Thr Leu Gly His Arg Asn Pro Gln
                245                 250                 255

Gly Leu Ala Phe Thr Pro Asn Gly Lys Leu Leu Gln Ser Glu Gln Gly
            260                 265                 270

Pro Asn Ser Asp Asp Glu Ile Asn Leu Ile Val Lys Gly Gly Asn Tyr
        275                 280                 285
```

```
Gly Trp Pro Asn Val Ala Gly Tyr Lys Asp Asp Ser Gly Tyr Ala Tyr
290                 295                 300
Ala Asn Tyr Ser Ala Ala Ser Asn Lys Ala Gln Ile Lys Asp Leu Gly
305                 310                 315                 320
Gln Asn Gly Leu Lys Val Ala Ala Gly Val Pro Val Thr Lys Glu Ser
                325                 330                 335
Glu Trp Thr Gly Lys Asn Phe Val Pro Pro Leu Lys Thr Leu Tyr Thr
            340                 345                 350
Val Gln Asp Thr Tyr Asn Tyr Asn Asp Pro Thr Cys Gly Asp Met Thr
        355                 360                 365
Tyr Ile Cys Trp Pro Thr Val Ala Pro Ser Ser Ala Tyr Val Tyr Lys
370                 375                 380
Gly Gly Lys Lys Ala Ile Ser Gly Trp Glu Asn Thr Leu Leu Val Pro
385                 390                 395                 400
Ser Leu Lys Arg Gly Val Ile Phe Arg Ile Lys Leu Asp Pro Thr Tyr
                405                 410                 415
Ser Ala Thr Tyr Asp Asp Ala Val Pro Met Phe Lys Ser Asn Asn Arg
            420                 425                 430
Tyr Arg Asp Val Ile Ala Ser Pro Asp Gly Asn Val Leu Tyr Val Leu
        435                 440                 445
Thr Asp Thr Ser Gly Asn Val Gln Lys Asp Asp Gly Ser Val Thr Asn
450                 455                 460
Thr Leu Glu Asn Pro Gly Ser Leu Ile Lys Phe Thr Tyr Lys Ala Lys
465                 470                 475                 480
```

<210> SEQ ID NO 4
<211> LENGTH: 1443
<212> TYPE: DNA
<213> ORGANISM: Acinetobacter calcoaceticus

<400> SEQUENCE: 4

| | | | | | |
|---|---|---|---|---|---|
| atgaataaac | atttattggc | taaaattact | ttattaggcg | ctgctcagct | acttacgctc | 60 |
| aattcagcat | tgctgatgt | tcctcttaca | ccatctcaat | tgctaaagc | gaaaacagaa | 120 |
| agctttgaca | agaaagttct | tctatctaat | ttaaataagc | cacatgcttt | gttgtggggg | 180 |
| cctgataatc | aaatttggtt | aacggagcgg | gcaacaggga | agattctaag | agtgaatcca | 240 |
| gagtcgggca | gtgtaaaaac | agttttttcag | gttcctgaga | ttgtaaatga | tgctgatgga | 300 |
| caaaacggtt | tattgggttt | tgcctttcat | cctgacttta | aaaataatcc | ttatatctat | 360 |
| gtttcaggta | cttttaaaaa | tccgaaatct | acagataaag | aattaccgaa | tcaaactatt | 420 |
| attcgtcgat | ataccctataa | caaagcaaca | gatactcttg | agaaaccagt | agatttatta | 480 |
| gcaggattac | cttcatcgaa | agaccatcag | tcgggtcgcc | ttgtcattgg | tccagaccaa | 540 |
| aagatttact | atacgattgg | tgatcagggg | cgtaaccagc | tggcttattt | attcttacca | 600 |
| aatcaagcac | agcatacgcc | gactcaacag | gaactgagcg | gcaaagacta | tcatacctat | 660 |
| atgggtaaag | tattacgctt | aaatctggat | ggaagtattc | caaaagataa | tccaagcttt | 720 |
| aacggtgtaa | ttagccatat | tatacgctc | ggtcatcgta | tccacagggg | cttggcattt | 780 |
| actccaaatg | gtaaactgtt | gcaatctgaa | cagggtccaa | actctgacga | tgaaattaac | 840 |
| ctcattgtca | aggtggtaa | ctatggctgg | ccaaatgtag | cgggttataa | agatgatagt | 900 |
| ggttatgcct | atgcaaatta | ttcggcagca | agcaataaag | cacaaattaa | agatttagga | 960 |
| caaaatggtt | taaagtggc | agctggcgtt | ccagtgacta | agagtctga | atggactggt | 1020 |
| aaaaactttg | taccgccgtt | aaaaacttta | tataccgtcc | aagataccta | aactataat | 1080 |

-continued

```
gacccaacct gtggggatat gacctacatt tgctggccaa cggttgcgcc gtcatctgct    1140
tatgtctata agggaggcaa aaaagcaatt tctggttggg aaaataccttt attggttcca    1200 tctttaaagc gcggtgttat tttccgtatt aagctagatc caacttacag tgctacttat    1260
gatgatgctg tgccgatgtt aagagcaac aatcgttatc gtgacgtgat tgcaagtcca    1320
gatggaaatg ttttatatgt attgactgat acttccggaa atgtccaaaa agatgatggt    1380
tctgtaacga atacattaga aaacccagga tctctcatta agttcaccta taaggctaag    1440
taa                                                                 1443
```

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence : sense primer

<400> SEQUENCE: 5

```
acaaatcata tagagaactc g                                              21
```

<210> SEQ ID NO 6
<211> LENGTH: 40
<212> TYPE: DNA
<213> ORGANISM: Artificial Sequence
<220> FEATURE:
<223> OTHER INFORMATION: Description of Artificial Sequence : antisense primer

<400> SEQUENCE: 6

```
ttacttagcc ttataggtga acttaatgag agatcctggg                          40
```

<210> SEQ ID NO 7
<211> LENGTH: 48
<212> TYPE: DNA
<213> ORGANISM: Artificial Sequence
<220> FEATURE:
<223> OTHER INFORMATION: Description of Artificial Sequence : sense primer

<400> SEQUENCE: 7

```
gcggccgcga attcatgaat aaacatttat tggctaaaat tactttat                 48
```

<210> SEQ ID NO 8
<211> LENGTH: 57
<212> TYPE: DNA
<213> ORGANISM: Artificial Sequence
<220> FEATURE:
<223> OTHER INFORMATION: Description of Artificial Sequence : antisense primer

<400> SEQUENCE: 8

```
gcggccgcct gcagctatta cttagcctta taggtgaact taatgagaga tcctggg      57
```

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence : sense primer

<400> SEQUENCE: 9

```
tcacatgttc tttcctgcgt tatc                                           24
```

<210> SEQ ID NO 10
<211> LENGTH: 46
<212> TYPE: DNA
<213> ORGANISM: Artificial Sequence
<220> FEATURE:
<223> OTHER INFORMATION: Description of Artificial Sequence : antisense
      primer

<400> SEQUENCE: 10
atggtgatgg tgatggtgct tagccttata ggtgaactta atgaga          46

<210> SEQ ID NO 11
<211> LENGTH: 42
<212> TYPE: DNA
<213> ORGANISM: Artificial Sequence
<220> FEATURE:
<223> OTHER INFORMATION: Description of Artificial Sequence : antisense
      primer

<400> SEQUENCE: 11
gcggccgcct gcagctatta atggtgatgg tgcttagcct ta              42

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence : antisense
      primer

<400> SEQUENCE: 12
ggcgcgtact atggttgctt tga                                   23

<210> SEQ ID NO 13
<211> LENGTH: 35
<212> TYPE: DNA
<213> ORGANISM: Artificial Sequence
<220> FEATURE:
<223> OTHER INFORMATION: Description of Artificial Sequence : sense
      primer GDHB/G75-F
<220> FEATURE:
<221> NAME/KEY: misc_feature
<222> LOCATION: (16)..(18)
<223> OTHER INFORMATION: n stands for any base

<400> SEQUENCE: 13
gtaaatgatg ctgatnnnca aaacggttta ttggg                      35

<210> SEQ ID NO 14
<211> LENGTH: 35
<212> TYPE: DNA
<213> ORGANISM: Artificial Sequence
<220> FEATURE:
<223> OTHER INFORMATION: Description of Artificial Sequence : antisense
      primer GDHB/G75-R
<220> FEATURE:
<221> NAME/KEY: misc_feature
<222> LOCATION: (18)..(20)
<223> OTHER INFORMATION: n stands for any base

<400> SEQUENCE: 14
cccaataaac cgttttgnnn atcagcatca tttac                      35

<210> SEQ ID NO 15
<211> LENGTH: 38
<212> TYPE: DNA
<213> ORGANISM: Artificial Sequence

```
<220> FEATURE:
<223> OTHER INFORMATION: Description of Artificial Sequence : sense
      primer GDHB/G295-F
<220> FEATURE:
<221> NAME/KEY: misc_feature
<222> LOCATION: (16)..(18)
<223> OTHER INFORMATION: n stands for any base

<400> SEQUENCE: 15
caaattaaag atttannnca aaatggttta aaagtggc                              38

<210> SEQ ID NO 16
<211> LENGTH: 38
<212> TYPE: DNA
<213> ORGANISM: Artificial Sequence
<220> FEATURE:
<223> OTHER INFORMATION: Description of Artificial Sequence : antisense
      primer GDHB/G295-R
<220> FEATURE:
<221> NAME/KEY: misc_feature
<222> LOCATION: (21)..(23)
<223> OTHER INFORMATION: n stands for any base

<400> SEQUENCE: 16
gccactttta aaccattttg nnntaaatct ttaatttg                              38

<210> SEQ ID NO 17
<211> LENGTH: 33
<212> TYPE: DNA
<213> ORGANISM: Artificial Sequence
<220> FEATURE:
<223> OTHER INFORMATION: Description of Artificial Sequence : sense
      primer GDHB/M342-F
<220> FEATURE:
<221> NAME/KEY: misc_feature
<222> LOCATION: (16)..(18)
<223> OTHER INFORMATION: n stands for any base

<400> SEQUENCE: 17
ccaacctgtg gggatnnnac ctacatttgc tgg                                   33

<210> SEQ ID NO 18
<211> LENGTH: 33
<212> TYPE: DNA
<213> ORGANISM: Artificial Sequence
<220> FEATURE:
<223> OTHER INFORMATION: Description of Artificial Sequence : antisense
      primer GDHB/M342-R
<220> FEATURE:
<221> NAME/KEY: misc_feature
<222> LOCATION: (16)..(18)
<223> OTHER INFORMATION: n stands for any base

<400> SEQUENCE: 18
ccagcaaatg taggtnnnat ccccacaggt tgg                                   33

<210> SEQ ID NO 19
<211> LENGTH: 33
<212> TYPE: DNA
<213> ORGANISM: Artificial Sequence
<220> FEATURE:
<223> OTHER INFORMATION: Description of Artificial Sequence : sense
      primer GDHB/A351-F
<220> FEATURE:
<221> NAME/KEY: misc_feature
<222> LOCATION: (11)..(13)
<223> OTHER INFORMATION: n stands for any base

<400> SEQUENCE: 19
gccaacggtt nnnccgtcat ctgcttatgt cta                                   33
```

<210> SEQ ID NO 20
<211> LENGTH: 33
<212> TYPE: DNA
<213> ORGANISM: Artificial Sequence
<220> FEATURE:
<223> OTHER INFORMATION: Description of Artificial Sequence : sense
      primer GDHB/A351-R
<220> FEATURE:
<221> NAME/KEY: misc_feature
<222> LOCATION: (21)..(23)
<223> OTHER INFORMATION: n stands for any base

<400> SEQUENCE: 20
tagacataag cagatgacgg nnnaaccgtt ggc                            33

<210> SEQ ID NO 21
<211> LENGTH: 33
<212> TYPE: DNA
<213> ORGANISM: Artificial Sequence
<220> FEATURE:
<223> OTHER INFORMATION: Description of Artificial Sequence : antisense
      primer GDHB/Q168-F
<220> FEATURE:
<221> NAME/KEY: misc_feature
<222> LOCATION: (16)..(18)
<223> OTHER INFORMATION: n stands for any base

<400> SEQUENCE: 21
gatcaggggc gtaacnnnct ggcttattta ttc                            33

<210> SEQ ID NO 22
<211> LENGTH: 33
<212> TYPE: DNA
<213> ORGANISM: Artificial Sequence
<220> FEATURE:
<223> OTHER INFORMATION: Description of Artificial Sequence : sense
      primer GDHB/Q168-F
<220> FEATURE:
<221> NAME/KEY: misc_feature
<222> LOCATION: (16)..(18)
<223> OTHER INFORMATION: n stands for any base

<400> SEQUENCE: 22
gaataaataa gccagnnngt tacgcccctg atc                            33

<210> SEQ ID NO 23
<211> LENGTH: 33
<212> TYPE: DNA
<213> ORGANISM: Artificial Sequence
<220> FEATURE:
<223> OTHER INFORMATION: Description of Artificial Sequence : sense
      primer GDHB/L169-F
<220> FEATURE:
<221> NAME/KEY: misc_feature
<222> LOCATION: (14)..(16)
<223> OTHER INFORMATION: n stands for any base

<400> SEQUENCE: 23
ggggcgtaac cagnnngctt atttattctt acc                            33

<210> SEQ ID NO 24
<211> LENGTH: 33
<212> TYPE: DNA
<213> ORGANISM: Artificial Sequence
<220> FEATURE:
<223> OTHER INFORMATION: Description of Artificial Sequence : antisense
      primer GDHB/L169-R
<220> FEATURE:
<221> NAME/KEY: misc_feature

```
<222> LOCATION: (18)..(20)
<223> OTHER INFORMATION: n stands for any base

<400> SEQUENCE: 24
ggtaagaata aataagcnnn ctggttacgc ccc                                33

<210> SEQ ID NO 25
<211> LENGTH: 37
<212> TYPE: DNA
<213> ORGANISM: Artificial Sequence
<220> FEATURE:
<223> OTHER INFORMATION: Description of Artificial Sequence : sense
      primer GDHB/W347-F
<220> FEATURE:
<221> NAME/KEY: misc_feature
<222> LOCATION: (20)..(22)
<223> OTHER INFORMATION: n stands for any base

<400> SEQUENCE: 25
ggatatgacc tacatttgcn nnccaacggt tgcgccg                            37

<210> SEQ ID NO 26
<211> LENGTH: 37
<212> TYPE: DNA
<213> ORGANISM: Artificial Sequence
<220> FEATURE:
<223> OTHER INFORMATION: Description of Artificial Sequence : antisense
      primer GDHB/W347-R
<220> FEATURE:
<221> NAME/KEY: misc_feature
<222> LOCATION: (16)..(18)
<223> OTHER INFORMATION: n stands for any base

<400> SEQUENCE: 26
cggcgcaacc gttggnnngc aaatgtaggt catatcc                            37

<210> SEQ ID NO 27
<211> LENGTH: 35
<212> TYPE: DNA
<213> ORGANISM: Artificial Sequence
<220> FEATURE:
<223> OTHER INFORMATION: Description of Artificial Sequence : antisense
      primer

<400> SEQUENCE: 27
aagaataaat aagccagttg gttacgcccc tgatc                              35

<210> SEQ ID NO 28
<211> LENGTH: 455
<212> TYPE: PRT
<213> ORGANISM: Acinetobacter calcoaceticus
<220> FEATURE:
<221> NAME/KEY: MUTAGEN
<222> LOCATION: (169)..(169)
<223> OTHER INFORMATION:
<220> FEATURE:
<221> NAME/KEY: MUTAGEN
<222> LOCATION: (295)..(295)
<223> OTHER INFORMATION:
<220> FEATURE:
<221> NAME/KEY: MUTAGEN
<222> LOCATION: (342)..(342)
<223> OTHER INFORMATION:
<220> FEATURE:
<221> NAME/KEY: MUTAGEN
<222> LOCATION: (351)..(351)
<223> OTHER INFORMATION:

<400> SEQUENCE: 28

Asp Val Pro Leu Thr Pro Ser Gln Phe Ala Lys Ala Lys Thr Glu Ser
```

-continued

```
  1               5              10              15
Phe Asp Lys Lys Val Leu Leu Ser Asn Leu Asn Lys Pro His Ala Leu
             20              25              30
Leu Trp Gly Pro Asp Asn Gln Ile Trp Leu Thr Glu Arg Ala Thr Gly
             35              40              45
Lys Ile Leu Arg Val Asn Pro Glu Ser Gly Ser Val Lys Thr Val Phe
             50              55              60
Gln Val Pro Glu Ile Val Asn Asp Ala Asp Gly Gln Asn Gly Leu Leu
 65              70              75              80
Gly Phe Ala Phe His Pro Asp Phe Lys Asn Asn Pro Tyr Ile Tyr Val
                 85              90              95
Ser Gly Thr Phe Lys Asn Pro Lys Ser Thr Asp Lys Glu Leu Pro Asn
                100             105             110
Gln Thr Ile Ile Arg Arg Tyr Thr Tyr Asn Lys Ala Thr Asp Thr Leu
                115             120             125
Glu Lys Pro Val Asp Leu Leu Ala Gly Leu Pro Ser Ser Lys Asp His
             130             135             140
Gln Ser Gly Arg Leu Val Ile Gly Pro Asp Gln Lys Ile Tyr Tyr Thr
145             150             155             160
Ile Gly Asp Gln Gly Arg Asn Gln Phe Ala Tyr Leu Phe Leu Pro Asn
                165             170             175
Gln Ala Gln His Thr Pro Thr Gln Gln Glu Leu Ser Gly Lys Asp Tyr
                180             185             190
His Thr Tyr Met Gly Lys Val Leu Arg Leu Asn Leu Asp Gly Ser Ile
                195             200             205
Pro Lys Asp Asn Pro Ser Phe Asn Gly Val Ile Ser His Ile Tyr Thr
             210             215             220
Leu Gly His Arg Asn Pro Gln Gly Leu Ala Phe Thr Pro Asn Gly Lys
225             230             235             240
Leu Leu Gln Ser Glu Gln Gly Pro Asn Ser Asp Asp Glu Ile Asn Leu
                245             250             255
Ile Val Lys Gly Gly Asn Tyr Gly Trp Pro Asn Val Ala Gly Tyr Lys
                260             265             270
Asp Asp Ser Gly Tyr Ala Tyr Ala Asn Tyr Ser Ala Ala Ser Asn Lys
                275             280             285
Ala Gln Ile Lys Asp Leu Glu Gln Asn Gly Leu Lys Val Ala Ala Gly
             290             295             300
Val Pro Val Thr Lys Glu Ser Glu Trp Thr Gly Lys Asn Phe Val Pro
305             310             315             320
Pro Leu Lys Thr Leu Tyr Thr Val Gln Asp Thr Tyr Asn Tyr Asn Asp
                325             330             335
Pro Thr Cys Gly Asp Pro Thr Tyr Ile Cys Trp Pro Thr Val Thr Pro
                340             345             350
Ser Ser Ala Tyr Val Tyr Lys Gly Gly Lys Ala Ile Ser Gly Trp
                355             360             365
Glu Asn Thr Leu Leu Val Pro Ser Leu Lys Arg Gly Val Ile Phe Arg
             370             375             380
Ile Lys Leu Asp Pro Thr Tyr Ser Ala Thr Tyr Asp Asp Ala Val Pro
385             390             395             400
Met Phe Lys Ser Asn Asn Arg Tyr Arg Asp Val Ile Ala Ser Pro Asp
                405             410             415
Gly Asn Val Leu Tyr Val Leu Thr Asp Thr Ser Gly Asn Val Gln Lys
             420             425             430
```

```
Asp Asp Gly Ser Val Thr Asn Thr Leu Glu Asn Pro Gly Ser Leu Ile
        435                 440                 445

Lys Phe Thr Tyr Lys Ala Lys
        450                 455

<210> SEQ ID NO 29
<211> LENGTH: 455
<212> TYPE: PRT
<213> ORGANISM: Acinetobacter calcoaceticus
<220> FEATURE:
<221> NAME/KEY: MUTAGEN
<222> LOCATION: (295)..(295)
<223> OTHER INFORMATION:
<220> FEATURE:
<221> NAME/KEY: MUTAGEN
<222> LOCATION: (351)..(351)
<223> OTHER INFORMATION:

<400> SEQUENCE: 29

Asp Val Pro Leu Thr Pro Ser Gln Phe Ala Lys Ala Lys Thr Glu Ser
1               5                   10                  15

Phe Asp Lys Lys Val Leu Leu Ser Asn Leu Asn Lys Pro His Ala Leu
            20                  25                  30

Leu Trp Gly Pro Asp Asn Gln Ile Trp Leu Thr Glu Arg Ala Thr Gly
        35                  40                  45

Lys Ile Leu Arg Val Asn Pro Glu Ser Gly Ser Val Lys Thr Val Phe
    50                  55                  60

Gln Val Pro Glu Ile Val Asn Asp Ala Asp Gly Gln Asn Gly Leu Leu
65                  70                  75                  80

Gly Phe Ala Phe His Pro Asp Phe Lys Asn Asn Pro Tyr Ile Tyr Val
                85                  90                  95

Ser Gly Thr Phe Lys Asn Pro Lys Ser Thr Asp Lys Glu Leu Pro Asn
            100                 105                 110

Gln Thr Ile Ile Arg Arg Tyr Thr Tyr Asn Lys Ala Thr Asp Thr Leu
        115                 120                 125

Glu Lys Pro Val Asp Leu Leu Ala Gly Leu Pro Ser Ser Lys Asp His
130                 135                 140

Gln Ser Gly Arg Leu Val Ile Gly Pro Asp Gln Lys Ile Tyr Tyr Thr
145                 150                 155                 160

Ile Gly Asp Gln Gly Arg Asn Gln Leu Ala Tyr Leu Phe Leu Pro Asn
                165                 170                 175

Gln Ala Gln His Thr Pro Thr Gln Gln Glu Leu Ser Gly Lys Asp Tyr
            180                 185                 190

His Thr Tyr Met Gly Lys Val Leu Arg Leu Asn Leu Asp Gly Ser Ile
        195                 200                 205

Pro Lys Asp Asn Pro Ser Phe Asn Gly Val Ile Ser His Ile Tyr Thr
    210                 215                 220

Leu Gly His Arg Asn Pro Gln Gly Leu Ala Phe Thr Pro Asn Gly Lys
225                 230                 235                 240

Leu Leu Gln Ser Glu Gln Gly Pro Asn Ser Asp Asp Glu Ile Asn Leu
                245                 250                 255

Ile Val Lys Gly Gly Asn Tyr Gly Trp Pro Asn Val Ala Gly Tyr Lys
            260                 265                 270

Asp Asp Ser Gly Tyr Ala Tyr Ala Asn Tyr Ser Ala Ala Ser Asn Lys
        275                 280                 285

Ala Gln Ile Lys Asp Leu Asp Gln Asn Gly Leu Lys Val Ala Ala Gly
    290                 295                 300
```

```
Val Pro Val Thr Lys Glu Ser Glu Trp Thr Gly Lys Asn Phe Val Pro
305                 310                 315                 320

Pro Leu Lys Thr Leu Tyr Thr Val Gln Asp Thr Tyr Asn Tyr Asn Asp
            325                 330                 335

Pro Thr Cys Gly Asp Met Thr Tyr Ile Cys Trp Pro Thr Val Thr Pro
        340                 345                 350

Ser Ser Ala Tyr Val Tyr Lys Gly Gly Lys Lys Ala Ile Ser Gly Trp
        355                 360                 365

Glu Asn Thr Leu Leu Val Pro Ser Leu Lys Arg Gly Val Ile Phe Arg
370                 375                 380

Ile Lys Leu Asp Pro Thr Tyr Ser Ala Thr Tyr Asp Asp Ala Val Pro
385                 390                 395                 400

Met Phe Lys Ser Asn Asn Arg Tyr Arg Asp Val Ile Ala Ser Pro Asp
            405                 410                 415

Gly Asn Val Leu Tyr Val Leu Thr Asp Thr Ser Gly Asn Val Gln Lys
            420                 425                 430

Asp Asp Gly Ser Val Thr Asn Thr Leu Glu Asn Pro Gly Ser Leu Ile
            435                 440                 445

Lys Phe Thr Tyr Lys Ala Lys
450                 455
```

```
<210> SEQ ID NO 30
<211> LENGTH: 455
<212> TYPE: PRT
<213> ORGANISM: Acinetobacter calcoaceticus
<220> FEATURE:
<221> NAME/KEY: MUTAGEN
<222> LOCATION: (295)..(295)
<223> OTHER INFORMATION:
<220> FEATURE:
<221> NAME/KEY: MUTAGEN
<222> LOCATION: (342)..(342)
<223> OTHER INFORMATION:
<220> FEATURE:
<221> NAME/KEY: MUTAGEN
<222> LOCATION: (351)..(351)
<223> OTHER INFORMATION:

<400> SEQUENCE: 30

Asp Val Pro Leu Thr Pro Ser Gln Phe Ala Lys Ala Lys Thr Glu Ser
1               5                   10                  15

Phe Asp Lys Lys Val Leu Leu Ser Asn Leu Asn Lys Pro His Ala Leu
            20                  25                  30

Leu Trp Gly Pro Asp Asn Gln Ile Trp Leu Thr Glu Arg Ala Thr Gly
        35                  40                  45

Lys Ile Leu Arg Val Asn Pro Glu Ser Gly Ser Val Lys Thr Val Phe
50                  55                  60

Gln Val Pro Glu Ile Val Asn Asp Ala Asp Gly Gln Asn Gly Leu Leu
65                  70                  75                  80

Gly Phe Ala Phe His Pro Asp Phe Lys Asn Asn Pro Tyr Ile Tyr Val
            85                  90                  95

Ser Gly Thr Phe Lys Asn Pro Lys Ser Thr Asp Lys Glu Leu Pro Asn
            100                 105                 110

Gln Thr Ile Ile Arg Arg Tyr Thr Tyr Asn Lys Ala Thr Asp Thr Leu
        115                 120                 125

Glu Lys Pro Val Asp Leu Leu Ala Gly Leu Pro Ser Ser Lys Asp His
130                 135                 140

Gln Ser Gly Arg Leu Val Ile Gly Pro Asp Gln Lys Ile Tyr Tyr Thr
```

```
                145                 150                 155                 160
Ile Gly Asp Gln Gly Arg Asn Gln Leu Ala Tyr Leu Phe Leu Pro Asn
                    165                 170                 175

Gln Ala Gln His Thr Pro Thr Gln Gln Glu Leu Ser Gly Lys Asp Tyr
                180                 185                 190

His Thr Tyr Met Gly Lys Val Leu Arg Leu Asn Leu Asp Gly Ser Ile
            195                 200                 205

Pro Lys Asp Asn Pro Ser Phe Asn Gly Val Ile Ser His Ile Tyr Thr
        210                 215                 220

Leu Gly His Arg Asn Pro Gln Gly Leu Ala Phe Thr Pro Asn Gly Lys
225                 230                 235                 240

Leu Leu Gln Ser Glu Gln Gly Pro Asn Ser Asp Asp Glu Ile Asn Leu
                245                 250                 255

Ile Val Lys Gly Gly Asn Tyr Gly Trp Pro Asn Val Ala Gly Tyr Lys
            260                 265                 270

Asp Asp Ser Gly Tyr Ala Tyr Ala Asn Tyr Ser Ala Ala Ser Asn Lys
        275                 280                 285

Ala Gln Ile Lys Asp Leu Tyr Gln Asn Gly Leu Lys Val Ala Ala Gly
    290                 295                 300

Val Pro Val Thr Lys Glu Ser Glu Trp Thr Gly Lys Asn Phe Val Pro
305                 310                 315                 320

Pro Leu Lys Thr Leu Tyr Thr Val Gln Asp Thr Tyr Asn Tyr Asn Asp
                325                 330                 335

Pro Thr Cys Gly Asp Pro Thr Tyr Ile Cys Trp Pro Thr Val Thr Pro
            340                 345                 350

Ser Ser Ala Tyr Val Tyr Lys Gly Gly Lys Lys Ala Ile Ser Gly Trp
        355                 360                 365

Glu Asn Thr Leu Leu Val Pro Ser Leu Lys Arg Gly Val Ile Phe Arg
    370                 375                 380

Ile Lys Leu Asp Pro Thr Tyr Ser Ala Thr Tyr Asp Asp Ala Val Pro
385                 390                 395                 400

Met Phe Lys Ser Asn Asn Arg Tyr Arg Asp Val Ile Ala Ser Pro Asp
                405                 410                 415

Gly Asn Val Leu Tyr Val Leu Thr Asp Thr Ser Gly Asn Val Gln Lys
            420                 425                 430

Asp Asp Gly Ser Val Thr Asn Thr Leu Glu Asn Pro Gly Ser Leu Ile
        435                 440                 445

Lys Phe Thr Tyr Lys Ala Lys
    450                 455

<210> SEQ ID NO 31
<211> LENGTH: 455
<212> TYPE: PRT
<213> ORGANISM: Acinetobacter calcoaceticus
<220> FEATURE:
<221> NAME/KEY: MUTAGEN
<222> LOCATION: (295)..(295)
<223> OTHER INFORMATION:
<220> FEATURE:
<221> NAME/KEY: MUTAGEN
<222> LOCATION: (342)..(342)
<223> OTHER INFORMATION:
<220> FEATURE:
<221> NAME/KEY: MUTAGEN
<222> LOCATION: (351)..(351)
<223> OTHER INFORMATION:

<400> SEQUENCE: 31
```

```
Asp Val Pro Leu Thr Pro Ser Gln Phe Ala Lys Ala Lys Thr Glu Ser
 1               5                  10                 15

Phe Asp Lys Lys Val Leu Leu Ser Asn Leu Asn Lys Pro His Ala Leu
             20                  25                  30

Leu Trp Gly Pro Asp Asn Gln Ile Trp Leu Thr Glu Arg Ala Thr Gly
             35                  40                  45

Lys Ile Leu Arg Val Asn Pro Glu Ser Gly Ser Val Lys Thr Val Phe
 50                  55                  60

Gln Val Pro Glu Ile Val Asn Asp Ala Asp Gly Gln Asn Gly Leu Leu
 65                  70                  75                  80

Gly Phe Ala Phe His Pro Asp Phe Lys Asn Asn Pro Tyr Ile Tyr Val
             85                  90                  95

Ser Gly Thr Phe Lys Asn Pro Lys Ser Thr Asp Lys Glu Leu Pro Asn
            100                 105                 110

Gln Thr Ile Ile Arg Arg Tyr Thr Tyr Asn Lys Ala Thr Asp Thr Leu
            115                 120                 125

Glu Lys Pro Val Asp Leu Leu Ala Gly Leu Pro Ser Ser Lys Asp His
        130                 135                 140

Gln Ser Gly Arg Leu Val Ile Gly Pro Asp Gln Lys Ile Tyr Tyr Thr
145                 150                 155                 160

Ile Gly Asp Gln Gly Arg Asn Gln Leu Ala Tyr Leu Phe Leu Pro Asn
                165                 170                 175

Gln Ala Gln His Thr Pro Thr Gln Gln Glu Leu Ser Gly Lys Asp Tyr
            180                 185                 190

His Thr Tyr Met Gly Lys Val Leu Arg Leu Asn Leu Asp Gly Ser Ile
            195                 200                 205

Pro Lys Asp Asn Pro Ser Phe Asn Gly Val Ile Ser His Ile Tyr Thr
        210                 215                 220

Leu Gly His Arg Asn Pro Gln Gly Leu Ala Phe Thr Pro Asn Gly Lys
225                 230                 235                 240

Leu Leu Gln Ser Glu Gln Gly Pro Asn Ser Asp Asp Glu Ile Asn Leu
                245                 250                 255

Ile Val Lys Gly Gly Asn Tyr Gly Trp Pro Asn Val Ala Gly Tyr Lys
            260                 265                 270

Asp Asp Ser Gly Tyr Ala Tyr Ala Asn Tyr Ser Ala Ala Ser Asn Lys
        275                 280                 285

Ala Gln Ile Lys Asp Leu Phe Gln Asn Gly Leu Lys Val Ala Ala Gly
        290                 295                 300

Val Pro Val Thr Lys Glu Ser Glu Trp Thr Gly Lys Asn Phe Val Pro
305                 310                 315                 320

Pro Leu Lys Thr Leu Tyr Thr Val Gln Asp Thr Tyr Asn Tyr Asn Asp
                325                 330                 335

Pro Thr Cys Gly Asp Pro Thr Tyr Ile Cys Trp Pro Thr Val Thr Pro
            340                 345                 350

Ser Ser Ala Tyr Val Tyr Lys Gly Gly Lys Lys Ala Ile Ser Gly Trp
            355                 360                 365

Glu Asn Thr Leu Leu Val Pro Ser Leu Lys Arg Gly Val Ile Phe Arg
        370                 375                 380

Ile Lys Leu Asp Pro Thr Tyr Ser Ala Thr Tyr Asp Asp Ala Val Pro
385                 390                 395                 400

Met Phe Lys Ser Asn Asn Arg Tyr Arg Asp Val Ile Ala Ser Pro Asp
                405                 410                 415

Gly Asn Val Leu Tyr Val Leu Thr Asp Thr Ser Gly Asn Val Gln Lys
```

```
                    420             425             430
Asp Asp Gly Ser Val Thr Asn Thr Leu Glu Asn Pro Gly Ser Leu Ile
        435                 440                 445

Lys Phe Thr Tyr Lys Ala Lys
    450                 455

<210> SEQ ID NO 32
<211> LENGTH: 455
<212> TYPE: PRT
<213> ORGANISM: Acinetobacter calcoaceticus
<220> FEATURE:
<221> NAME/KEY: MUTAGEN
<222> LOCATION: (169)..(169)
<223> OTHER INFORMATION:
<220> FEATURE:
<221> NAME/KEY: MUTAGEN
<222> LOCATION: (295)..(295)
<223> OTHER INFORMATION:
<220> FEATURE:
<221> NAME/KEY: MUTAGEN
<222> LOCATION: (342)..(342)
<223> OTHER INFORMATION:

<400> SEQUENCE: 32

Asp Val Pro Leu Thr Pro Ser Gln Phe Ala Lys Ala Lys Thr Glu Ser
1               5                   10                  15

Phe Asp Lys Lys Val Leu Leu Ser Asn Leu Asn Lys Pro His Ala Leu
            20                  25                  30

Leu Trp Gly Pro Asp Asn Gln Ile Trp Leu Thr Glu Arg Ala Thr Gly
        35                  40                  45

Lys Ile Leu Arg Val Asn Pro Glu Ser Gly Ser Val Lys Thr Val Phe
    50                  55                  60

Gln Val Pro Glu Ile Val Asn Asp Ala Asp Gly Gln Asn Gly Leu Leu
65                  70                  75                  80

Gly Phe Ala Phe His Pro Asp Phe Lys Asn Asn Pro Tyr Ile Tyr Val
                85                  90                  95

Ser Gly Thr Phe Lys Asn Pro Lys Ser Thr Asp Lys Glu Leu Pro Asn
            100                 105                 110

Gln Thr Ile Ile Arg Arg Tyr Thr Tyr Asn Lys Ala Thr Asp Thr Leu
        115                 120                 125

Glu Lys Pro Val Asp Leu Leu Ala Gly Leu Pro Ser Ser Lys Asp His
    130                 135                 140

Gln Ser Gly Arg Leu Val Ile Gly Pro Asp Gln Lys Ile Tyr Tyr Thr
145                 150                 155                 160

Ile Gly Asp Gln Gly Arg Asn Gln Phe Ala Tyr Leu Phe Leu Pro Asn
                165                 170                 175

Gln Ala Gln His Thr Pro Thr Gln Gln Glu Leu Ser Gly Lys Asp Tyr
            180                 185                 190

His Thr Tyr Met Gly Lys Val Leu Arg Leu Asn Leu Asp Gly Ser Ile
        195                 200                 205

Pro Lys Asp Asn Pro Ser Phe Asn Gly Val Ile Ser His Ile Tyr Thr
    210                 215                 220

Leu Gly His Arg Asn Pro Gln Gly Leu Ala Phe Thr Pro Asn Gly Lys
225                 230                 235                 240

Leu Leu Gln Ser Glu Gln Gly Pro Asn Ser Asp Asp Glu Ile Asn Leu
                245                 250                 255

Ile Val Lys Gly Gly Asn Tyr Gly Trp Pro Asn Val Ala Gly Tyr Lys
            260                 265                 270
```

-continued

```
Asp Asp Ser Gly Tyr Ala Tyr Asn Tyr Ser Ala Ala Ser Asn Lys
        275                 280                 285

Ala Gln Ile Lys Asp Leu Glu Gln Asn Gly Leu Lys Val Ala Ala Gly
    290                 295                 300

Val Pro Val Thr Lys Glu Ser Glu Trp Thr Gly Lys Asn Phe Val Pro
305                 310                 315                 320

Pro Leu Lys Thr Leu Tyr Thr Val Gln Asp Thr Tyr Asn Tyr Asn Asp
                325                 330                 335

Pro Thr Cys Gly Asp Pro Thr Tyr Ile Cys Trp Pro Thr Val Ala Pro
            340                 345                 350

Ser Ser Ala Tyr Val Tyr Lys Gly Lys Lys Ala Ile Ser Gly Trp
        355                 360                 365

Glu Asn Thr Leu Leu Val Pro Ser Leu Lys Arg Gly Val Ile Phe Arg
    370                 375                 380

Ile Lys Leu Asp Pro Thr Tyr Ser Ala Thr Tyr Asp Ala Val Pro
385                 390                 395                 400

Met Phe Lys Ser Asn Asn Arg Tyr Arg Asp Val Ile Ala Ser Pro Asp
                405                 410                 415

Gly Asn Val Leu Tyr Val Leu Thr Asp Thr Ser Gly Asn Val Gln Lys
            420                 425                 430

Asp Asp Gly Ser Val Thr Asn Thr Leu Glu Asn Pro Gly Ser Leu Ile
        435                 440                 445

Lys Phe Thr Tyr Lys Ala Lys
        450                 455

<210> SEQ ID NO 33
<211> LENGTH: 455
<212> TYPE: PRT
<213> ORGANISM: Acinetobacter calcoaceticus
<220> FEATURE:
<221> NAME/KEY: MUTAGEN
<222> LOCATION: (75)..(75)
<223> OTHER INFORMATION:
<220> FEATURE:
<221> NAME/KEY: MUTAGEN
<222> LOCATION: (295)..(295)
<223> OTHER INFORMATION:
<220> FEATURE:
<221> NAME/KEY: MUTAGEN
<222> LOCATION: (342)..(342)
<223> OTHER INFORMATION:
<220> FEATURE:
<221> NAME/KEY: MUTAGEN
<222> LOCATION: (351)..(351)
<223> OTHER INFORMATION:

<400> SEQUENCE: 33

Asp Val Pro Leu Thr Pro Ser Gln Phe Ala Lys Ala Lys Thr Glu Ser
1               5                   10                  15

Phe Asp Lys Lys Val Leu Leu Ser Asn Leu Asn Lys Pro His Ala Leu
            20                  25                  30

Leu Trp Gly Pro Asp Asn Gln Ile Trp Leu Thr Glu Arg Ala Thr Gly
        35                  40                  45

Lys Ile Leu Arg Val Asn Pro Glu Ser Gly Ser Val Lys Thr Val Phe
    50                  55                  60

Gln Val Pro Glu Ile Val Asn Asp Ala Asp Trp Gln Asn Gly Leu Leu
65                  70                  75                  80

Gly Phe Ala Phe His Pro Asp Phe Lys Asn Asn Pro Tyr Ile Tyr Val
                85                  90                  95

Ser Gly Thr Phe Lys Asn Pro Lys Ser Thr Asp Lys Glu Leu Pro Asn
```

```
                100                 105                 110
Gln Thr Ile Ile Arg Arg Tyr Thr Tyr Asn Lys Ala Thr Asp Thr Leu
        115                 120                 125

Glu Lys Pro Val Asp Leu Leu Ala Gly Leu Pro Ser Ser Lys Asp His
130                 135                 140

Gln Ser Gly Arg Leu Val Ile Gly Pro Asp Gln Lys Ile Tyr Tyr Thr
145                 150                 155                 160

Ile Gly Asp Gln Gly Arg Asn Gln Leu Ala Tyr Leu Phe Leu Pro Asn
                165                 170                 175

Gln Ala Gln His Thr Pro Thr Gln Gln Glu Leu Ser Gly Lys Asp Tyr
            180                 185                 190

His Thr Tyr Met Gly Lys Val Leu Arg Leu Asn Leu Asp Gly Ser Ile
        195                 200                 205

Pro Lys Asp Asn Pro Ser Phe Asn Gly Val Ile Ser His Ile Tyr Thr
    210                 215                 220

Leu Gly His Arg Asn Pro Gln Gly Leu Ala Phe Thr Pro Asn Gly Lys
225                 230                 235                 240

Leu Leu Gln Ser Glu Gln Gly Pro Asn Ser Asp Asp Glu Ile Asn Leu
                245                 250                 255

Ile Val Lys Gly Gly Asn Tyr Gly Trp Pro Asn Val Ala Gly Tyr Lys
            260                 265                 270

Asp Asp Ser Gly Tyr Ala Tyr Ala Asn Tyr Ser Ala Ala Ser Asn Lys
        275                 280                 285

Ala Gln Ile Lys Asp Leu Glu Gln Asn Gly Leu Lys Val Ala Ala Gly
    290                 295                 300

Val Pro Val Thr Lys Glu Ser Glu Trp Thr Gly Lys Asn Phe Val Pro
305                 310                 315                 320

Pro Leu Lys Thr Leu Tyr Thr Val Gln Asp Thr Tyr Asn Tyr Asn Asp
                325                 330                 335

Pro Thr Cys Gly Asp Pro Thr Tyr Ile Cys Trp Pro Thr Val Thr Pro
            340                 345                 350

Ser Ser Ala Tyr Val Tyr Lys Gly Gly Lys Lys Ala Ile Ser Gly Trp
        355                 360                 365

Glu Asn Thr Leu Leu Val Pro Ser Leu Lys Arg Gly Val Ile Phe Arg
    370                 375                 380

Ile Lys Leu Asp Pro Thr Tyr Ser Ala Thr Tyr Asp Asp Ala Val Pro
385                 390                 395                 400

Met Phe Lys Ser Asn Asn Arg Tyr Arg Asp Val Ile Ala Ser Pro Asp
                405                 410                 415

Gly Asn Val Leu Tyr Val Leu Thr Asp Thr Ser Gly Asn Val Gln Lys
            420                 425                 430

Asp Asp Gly Ser Val Thr Asn Thr Leu Glu Asn Pro Gly Ser Leu Ile
        435                 440                 445

Lys Phe Thr Tyr Lys Ala Lys
    450                 455

<210> SEQ ID NO 34
<211> LENGTH: 455
<212> TYPE: PRT
<213> ORGANISM: Acinetobacter calcoaceticus
<220> FEATURE:
<221> NAME/KEY: MUTAGEN
<222> LOCATION: (342)..(342)
<223> OTHER INFORMATION:
<220> FEATURE:
<221> NAME/KEY: MUTAGEN
```

<222> LOCATION: (351)..(351)
<223> OTHER INFORMATION:

<400> SEQUENCE: 34

```
Asp Val Pro Leu Thr Pro Ser Gln Phe Ala Lys Ala Lys Thr Glu Ser
1               5                   10                  15

Phe Asp Lys Lys Val Leu Leu Ser Asn Leu Asn Lys Pro His Ala Leu
            20                  25                  30

Leu Trp Gly Pro Asp Asn Gln Ile Trp Leu Thr Glu Arg Ala Thr Gly
        35                  40                  45

Lys Ile Leu Arg Val Asn Pro Glu Ser Gly Ser Val Lys Thr Val Phe
50                  55                  60

Gln Val Pro Glu Ile Val Asn Asp Ala Asp Gly Gln Asn Gly Leu Leu
65                  70                  75                  80

Gly Phe Ala Phe His Pro Asp Phe Lys Asn Asn Pro Tyr Ile Tyr Val
            85                  90                  95

Ser Gly Thr Phe Lys Asn Pro Lys Ser Thr Asp Lys Glu Leu Pro Asn
            100                 105                 110

Gln Thr Ile Ile Arg Arg Tyr Thr Tyr Asn Lys Ala Thr Asp Thr Leu
        115                 120                 125

Glu Lys Pro Val Asp Leu Leu Ala Gly Leu Pro Ser Ser Lys Asp His
130                 135                 140

Gln Ser Gly Arg Leu Val Ile Gly Pro Asp Gln Lys Ile Tyr Tyr Thr
145                 150                 155                 160

Ile Gly Asp Gln Gly Arg Asn Gln Leu Ala Tyr Leu Phe Leu Pro Asn
            165                 170                 175

Gln Ala Gln His Thr Pro Thr Gln Gln Glu Leu Ser Gly Lys Asp Tyr
            180                 185                 190

His Thr Tyr Met Gly Lys Val Leu Arg Leu Asn Leu Asp Gly Ser Ile
        195                 200                 205

Pro Lys Asp Asn Pro Ser Phe Asn Gly Val Ile Ser His Ile Tyr Thr
210                 215                 220

Leu Gly His Arg Asn Pro Gln Gly Leu Ala Phe Thr Pro Asn Gly Lys
225                 230                 235                 240

Leu Leu Gln Ser Glu Gln Gly Pro Asn Ser Asp Asp Glu Ile Asn Leu
            245                 250                 255

Ile Val Lys Gly Gly Asn Tyr Gly Trp Pro Asn Val Ala Gly Tyr Lys
            260                 265                 270

Asp Asp Ser Gly Tyr Ala Tyr Ala Asn Tyr Ser Ala Ala Ser Asn Lys
        275                 280                 285

Ala Gln Ile Lys Asp Leu Gly Gln Asn Gly Leu Lys Val Ala Ala Gly
290                 295                 300

Val Pro Val Thr Lys Glu Ser Glu Trp Thr Gly Lys Asn Phe Val Pro
305                 310                 315                 320

Pro Leu Lys Thr Leu Tyr Thr Val Gln Asp Thr Tyr Asn Tyr Asn Asp
            325                 330                 335

Pro Thr Cys Gly Asp Pro Thr Tyr Ile Cys Trp Pro Thr Val Thr Pro
            340                 345                 350

Ser Ser Ala Tyr Val Tyr Lys Gly Gly Lys Lys Ala Ile Ser Gly Trp
        355                 360                 365

Glu Asn Thr Leu Leu Val Pro Ser Leu Lys Arg Gly Val Ile Phe Arg
        370                 375                 380

Ile Lys Leu Asp Pro Thr Tyr Ser Ala Thr Tyr Asp Asp Ala Val Pro
385                 390                 395                 400
```

```
Met Phe Lys Ser Asn Asn Arg Tyr Arg Asp Val Ile Ala Ser Pro Asp
            405                 410                 415

Gly Asn Val Leu Tyr Val Leu Thr Asp Thr Ser Gly Asn Val Gln Lys
            420                 425                 430

Asp Asp Gly Ser Val Thr Asn Thr Leu Glu Asn Pro Gly Ser Leu Ile
            435                 440                 445

Lys Phe Thr Tyr Lys Ala Lys
450                 455
```

PYRROLOQUINOLINE QUINONE-DEPENDENT GLUCOSE DEHYDROGENASE

FIELD OF THE INVENTION

The present invention relates to a pyrroloquinoline quinone-dependent glucose dehydrogenase. More particularly, the present invention relates to a modified pyrroloquinoline quinone-dependent glucose dehydrogenase in which an amino acid in a certain region is substituted by another amino acid as compared with a wild-type enzyme. The modified pyrroloquinoline quinone-dependent glucose dehydrogenase of the present invention is used for measurement of an amount of glucose in, for example, a clinical test.

BACKGROUND OF THE INVENTION

A pyrroloquinoline quinone-dependent β-D glucose dehydrogenase (EC1.1.199, PQQGDH) is conjugated with a coenzyme, pyrrolo-quinoline quinone (PQQ) to catalyze a reaction of oxidizing β-D glucose to produce gluconolactone. With this property, PQQGDH is used for determining an amount of glucose in a clinical test, a food analysis, monitoring of a culture process, and the like.

As examples of PQQGDH reported in the past, a PQQGDH produced by *Acinetobacter* species L.M.D 79.41 strain and a modified PQQGDH thereof are known (for example, JP 2000-312588A, JP 2000-350588A, JP 2000-197888A, JP 2001-346587A, WO02-34919 (A1), and A-M Cleton-Jansen et al., Mol. Gen. Genet., 217, 430 (1989)). The substrate specificity of the PQQGDH produced by L.M.D 79.41 strain is low. For example, also with respect to maltose, the reactivity of the PQQGDH has a reactivity corresponding to about 90% of the reactivity with respect to glucose.

SUMMARY OF THE INVENTION

In order to measure an exact amount of glucose, a PQQGDH is required to have high substrate specificity. For example, when carrying out diagnosis of diabetes for patients who undergo drip transfusion of blood, if PQQGDH having low substrate specificity is used, the obtained measurement value includes the amount of maltose in a transfusion liquid in addition to the amount of glucose. Thus, the exact amount of glucose in blood cannot be determined. Similarly, for example, when carrying out measurement for patients with hepatic disorder, if PQQGDH having low substrate specificity is used, due to the influence of galactose, reliable measurement may not be carried out. In this way, since PQQGDH having low substrate specificity is much influenced by other sugars such as maltose, an exact amount of glucose cannot be measured.

In the above-mentioned modified PQQGDH reported in the past, by substituting a part of amino acids of the wild-type PQQGDH, the substrate specificity is improved. However, reactivity with respect to maltose or galactose is still considerably remained. Therefore, further improvement of the substrate specificity for enabling the exact measurement of an amount of glucose has been desired. In particular, PQQGDH with sufficiently low reactivity with respect to galactose has not been found and been desired to be provided.

Under such circumstances, it is an object of the present invention to provide a modified PQQGDH having high substrate specificity with respect to glucose. In particular, it is an object of the present invention to provide a modified PQQGDH with extremely low reactivity with respect to galactose in addition to low reactivity with respect to maltose. Furthermore, the present invention also aims to provide polynucleotide, an expression vector and a transformant, which can be used for preparing the modified PQQGDH, and a method for preparing the modified PQQGDH using the polynucleotide, expression vector and transformant, and a kit for measuring glucose.

In order to achieve the above-mentioned objects, the present inventors have investigated in detail the relation between the substitution of amino acids in a certain region and the change in the substrate specificity in PQQGDH produced by *Acinetobacter calcoaceticus*. As a result, the present inventors succeeded in finding a plurality of regions deeply involved in the substrate specificity. That is to say, as mentioned in the below-mentioned Examples, the present inventors found that when the amino acid at position 351 was substituted in a wild-type PQQGDH of *Acinetobacter calcoaceticus*, the reactivity with respect to maltose and galactose was significantly lowered. Furthermore, the present inventors found that the amino acid at position 342 was also deeply involved in the substrate specificity. Herein, since these amino acids were located in a secondary structure including amino acid residues at positions 326 to 354, it was thought that by modifying this structural part, the substrate specificity with respect to glucose can be efficiently improved.

Furthermore, an amino acid residue at position 295 located in the secondary structure including amino acid residues at positions 278 to 320 was shown to be largely involved in the reactivity with respect to maltose and galactose. Thus, it was thought that the modification of this structural part was also effective for improving the specificity. Similarly, since it was observed that the substitution of the amino acid residue at position 169 also improved the substrate specificity, it was thought that the modification of the secondary structural part including amino acid residues at positions 162 to 197 was effective in improving the substrate specificity.

Furthermore, it was suggested that some other amino acid residues were involved in the substrate specificity.

Note here that the present inventors succeeded in obtaining various modified PQQGDHs in which amino acids were substituted in at least two or more positions 75, 168, 169, 295, 342, 347 and 351. In these modified PQQGDHs, the substrate specificity with respect to glucose was observed to be radically improved. In particular, it was clarified that in the modified PQQGDH in which amino acids at positions 169, 295, 342 and 351 were substituted had extremely low reactivity with respect to maltose and galactose. Similarly, it was clarified that the modified PQQGDH in which the amino acid at positions 342 and 351 were substituted also have extremely low reactivity with respect to maltose and galactose.

Herein, proteins having the same functions are generally similar to each other in structure of the region involved in its activity site or substrate specificity. Therefore, it is expected that the above-mentioned information as to the relation between the substitution of a certain amino acids and the substrate specificity in PQQGDH derived from *Acinetobacter* calcoaceticus may be applied to PQQGDH derived from other microorganisms.

The present invention was completed based on the above-mentioned findings and provides the following configurations.

[1] A modified pyrroloquinoline quinone-dependent glucose dehydrogenase, comprising an amino acid sequence in which one or more amino acids in a region corresponding to a first region consisting of amino acids at positions 326 to 354 in pyrroloquinoline quinone-dependent glucose dehydrogenase derived from *Acinetobacter calcoaceticus* are substituted as compared with an amino acid sequence of the corresponding wild-type enzyme.

[2] The modified pyrroloquinoline quinone-dependent glucose dehydrogenase described in [1], wherein in said region corresponding to the first region, two or more amino acids including amino acids corresponding to amino acids at positions 342 and 351 are substituted.

[3] A modified pyrroloquinoline quinone-dependent glucose dehydrogenase, comprising an amino acid sequence in which in a first region consisting of amino acids at positions 326 to 354 in the amino acid sequence of SEQ ID NO: 1, one or more amino acids are substituted by other amino acids.

[4] The modified pyrroloquinoline quinone-dependent glucose dehydrogenase described in [3], wherein in said first region, two or more amino acids including amino acids at positions 342 and 351 are substituted by other amino acids.

[5] A modified pyrroloquinoline quinone-dependent glucose dehydrogenase, comprising an amino acid sequence in which an amino acid corresponding to an amino acid at position 295 in pyrroloquinoline quinone-dependent glucose dehydrogenase derived from *Acinetobacter calcoaceticus* is substituted by another amino acid as compared with an amino acid sequence of the corresponding wild-type enzyme.

[6] A modified pyrroloquinoline quinone-dependent glucose dehydrogenase, comprising an amino acid sequence in which amino acids corresponding to amino acids of the following (1) and (2) in pyrroloquinoline quinone-dependent glucose dehydrogenase derived from *Acinetobacter calcoaceticus* are respectively substituted by other amino acids as compared with an amino acid sequence of the corresponding wild-type enzyme:
(1) an amino acid at position 295; and
(2) one or more amino acids selected from the group consisting of amino acids at positions 75, 168, 169, 342, 347 and 351.

[7] A modified pyrroloquinoline quinone-dependent glucose dehydrogenase, comprising any of the following amino acid sequences (1) to (6):
(1) an amino acid sequence in which amino acids corresponding to amino acids at positions 169, 295, 342 and 351 in pyrroloquinoline quinone-dependent glucose dehydrogenase derived from *Acinetobacter calcoaceticus* are respectively substituted by other amino acids, as compared with an amino acid sequence of the corresponding wild-type enzyme;
(2) an amino acid sequence in which amino acids corresponding to amino acids at positions 295 and 351 in pyrroloquinoline quinone-dependent glucose dehydrogenase derived from *Acinetobacter calcoaceticus* are respectively substituted by other amino acids, as compared with an amino acid sequence of the corresponding wild-type enzyme;
(3) an amino acid sequence in which amino acids corresponding to amino acids at positions 295, 342 and 351 in pyrroloquinoline quinone-dependent glucose dehydrogenase derived from *Acinetobacter calcoaceticus* are respectively substituted by other amino acids, as compared with an amino acid sequence of the corresponding wild-type enzyme;
(4) an amino acid sequence in which amino acids corresponding to amino acids at positions 169, 295 and 342 in pyrroloquinoline quinone-dependent glucose dehydrogenase derived from *Acinetobacter calcoaceticus* are respectively substituted by other amino acids, as compared with an amino acid sequence of the corresponding wild-type enzyme;
(5) an amino acid sequence in which amino acids corresponding to amino acids at positions 75, 295, 342 and 351 in pyrroloquinoline quinone-dependent glucose dehydrogenase derived from *Acinetobacter calcoaceticus* are respectively substituted by other amino acids, as compared with an amino acid sequence of the corresponding wild-type enzyme; and
(6) an amino acid sequence in which amino acids corresponding to amino acids at positions 342 and 351 in pyrroloquinoline quinone-dependent glucose dehydrogenase derived from *Acinetobacter calcoaceticus* are respectively substituted by other amino acids, as compared with an amino acid sequence of the corresponding wild-type enzyme.

[8] A modified pyrroloquinoline quinone-dependent glucose dehydrogenase, comprising any of the following amino acid sequences (1) to (6):
(1) an amino acid sequence of SEQ ID NO: 1 in which amino acids at positions 169, 295, 342 and 351 are substituted by other amino acids respectively;
(2) an amino acid sequence of SEQ ID NO: 1 in which amino acids at positions 295 and 351 are substituted by other amino acids respectively;
(3) an amino acid sequence of SEQ ID NO: 1 in which amino acids at positions 295, 342, and 351 are substituted by other amino acids respectively;
(4) an amino acid sequence of SEQ ID NO: 1 in which amino acids at positions 169, 295 and 342 are substituted by other amino acids respectively;
(5) an amino acid sequence of SEQ ID NO: 1 in which amino acids at positions 75, 295, 342 and 351 are substituted by other amino acids respectively; and
(6) an amino acid sequence of SEQ ID NO: 1 in which amino acids at positions 342 and 351 are substituted by other amino acids respectively.

[9] A modified pyrroloquinoline quinone-dependent glucose dehydrogenase, comprising any of amino acid sequences of SEQ ID NOs: 28 to 34.

[10] A modified pyrroloquinoline quinone-dependent glucose dehydrogenase, wherein the reactivity with respect to maltose is 40% or less and the reactivity with respect to galactose is 10% or less, respectively relative to the reactivity with respect to glucose.

[11] A modified pyrroloquinoline quinone-dependent glucose dehydrogenase, wherein the reactivity with respect to maltose is 20% or less and the reactivity with respect to galactose is 5% or less, respectively relative to the reactivity with respect to glucose.

[12] A modified pyrroloquinoline quinone-dependent glucose dehydrogenase, wherein the reactivity with respect to galactose is 10% or less relative to the reactivity with respect to glucose.

[13] An isolated polynucleotide encoding the modified pyrroloquinoline quinone-dependent glucose dehydrogenase described in any of [1] to [12].

[14] A vector containing polynucleotide described [13].

[15] A transformant holding polynucleotide described [13].

[16] A method for producing pyrroloquinoline quinone-dependent glucose dehydrogenase, the method comprising a step of culturing the transformant described in [15] in a state in which the polynucleotide can be expressed; and
a step of separating the expressed product of the polynucleotide.

[17] A kit for measuring glucose, comprising the modified pyrroloquinoline quinone-dependent glucose dehydrogenase described in any of [1] to [12].

The modified pyrroloquinoline quinone-dependent glucose dehydrogenase provided in the present invention has high specificity with respect to glucose. Therefore, by using such modified enzyme, an amount of glucose can be determined with high accuracy.

BRIEF DESCRIPTION OF THE DRAWINGS

These and other objects and technical advantages of the present invention will be readily apparent from the following description of the preferred exemplary embodiments of the invention in conjunction with the accompanying drawings, in which:

FIG. 1 shows a sequence (not including the signal region) of a gene encoding pyrroloquinoline quinone-dependent glucose dehydrogenase derived from the *Acinetobacter calcoaceticus* and an amino acid sequence (not including the signal region).

FIG. 2 shows a sequence (including the signal region) of a gene encoding pyrroloquinoline quinone-dependent glucose dehydrogenase derived from the *Acinetobacter calcoaceticus* and an amino acid sequence (including the signal region).

FIG. 4 is a table showing primers used in Mutation scrambling and the amplification sites.

FIG. 5 is a table showing a mixing ratio of each DNA fragment in Mutation scrambling. The setting bias rates are made to be 0.8 for G75, G295, M342 and 351, and 0.5 for Q168, L169 and W347, wherein the setting bias rate means a rate of amino acid substitution introduced by mutation scrambling.

FIG. 6 is a table showing positions of amino acid substitution and substrate specificity in various kinds of modified amino acid substitution obtained by mutation scrambling in Examples. Reactivities with respect to various substrates are shown by relative values when the reactivity with respect to glucose is represented by a value (100).

DETAILED DESCRIPTION OF THE INVENTION

Figure 3:
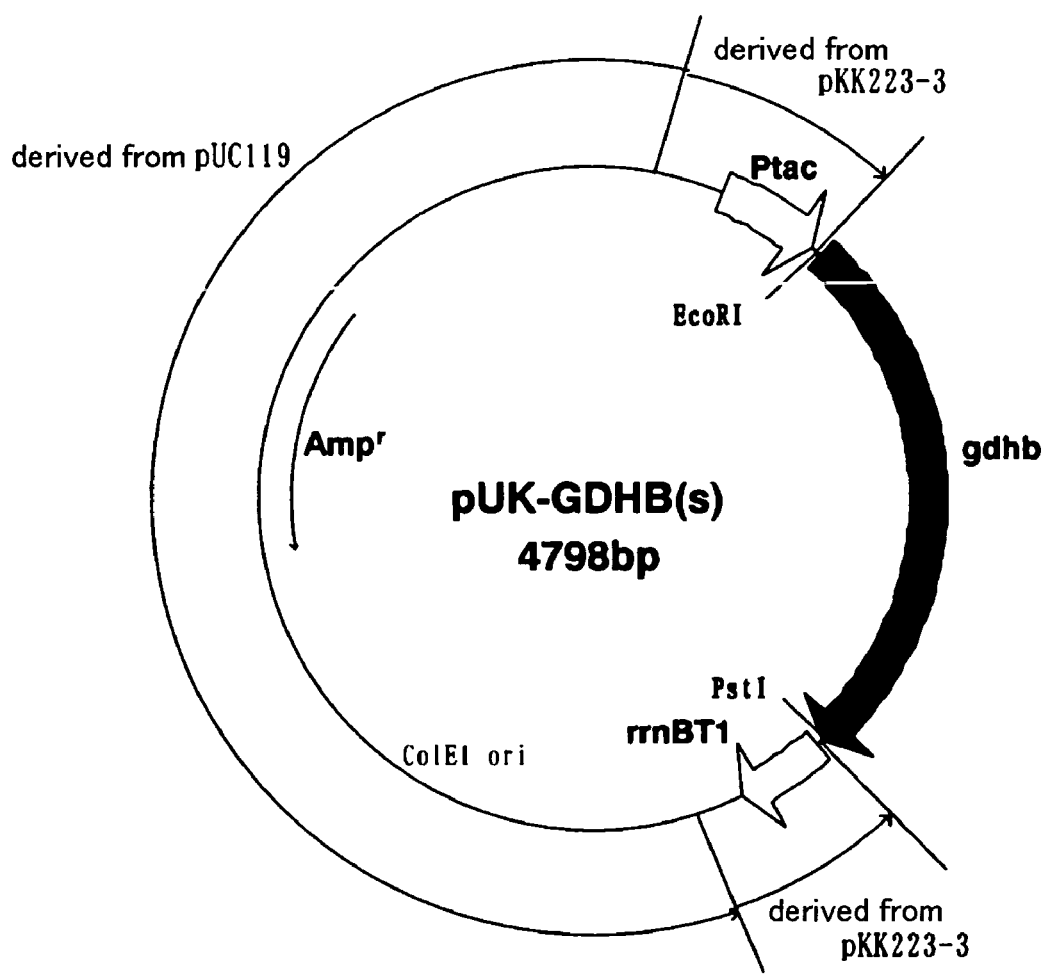
FIG. 3 shows a structure of an expression vector pUK-GDHB(S) used in Examples.

The present invention provides a modified PQQGDH in which an amino acid sequence in a certain region is substituted as compared with the corresponding wild-type enzyme. The modified PQQGDH of the present invention is typically prepared or designed by substituting a part of amino acids by another amino acids in naturally occurring PQQGDH, i.e., a wild-type PQQGDH. In this way, the wild-type PQQGDH which the modified PQQGDH of the present invention is based on (derived from) is herein denoted by "the corresponding wild-type enzyme." Examples of the wild-type enzyme of the present invention include a PQQGDH produced by oxidizing bacteria such as *Acinetobacter calcoaceticus*, *Acinetobacter baumannii*, *Pseudomonas aeruginosa*, *Pseudomonas putida*, *Pseudomonas fluorescens*, *Burkholderia cepacia*, *Gluconobacter oxydans*, *Acetobacter aceti*, etc., and *Agrobacterium radiobacter*, *Escherichia coli*, *Klebsiella aerogenes*, and the like.

The term "corresponding" used to explain an amino acid residue or region means that between proteins (enzymes) to be compared, the functions resulting from the structure are equal to each other, and particularly means that the functions in terms of the reactivity with respect to sugars other than glucose, for example, maltose, galactose, are equal. For example, in PQQGDH derived from microorganisms other than *Acinetobacter calcoaceticus*, when the primary structures of the PQQGDH derived from the other microorganisms is compared with that of the PQQGDH derived from *Acinetobacter calcoaceticus* and the homology in the secondary structures of both PQQGDHs are taken into consideration, a region of the PQQGDH derived from the other microorganisms which is reasonably thought to have the same function as one of the secondary structure regions of PQQGDH derived from *Acinetobacter calcoaceticus* can be referred to as "corresponding to the secondary structure region of PQQGDH derived from *Acinetobacter calcoaceticus*."

Positions of the amino acids in the present specification are specified by reference numbers sequentially given from the side of the N-terminal toward the C-terminal with asparatic acid at N-terminal given the reference number 1.

In one embodiment of the modified PQQGDH according to the present invention, as compared with the amino acid sequence of the corresponding wild-type enzyme, one or more amino acids are substituted by other amino acids in a region corresponding to a first region consisting of amino acids at positions 326 to 354 in pyrroloquinoline quinone-dependent glucose dehydrogenase derived from *Acinetobacter calcoaceticus* (hereinafter, referred to as "A. C. PQQGDH"). The amino acid sequence of A. C. PQQGDH in the present application is a sequence specified by SEQ ID NO: 1. This sequence is an amino acid sequence of PQQGDH produced by *Acinetobacter calcoaceticus* IFO 12552 strain as mentioned in Examples below.

In another embodiment of the modified PQQGDH of the present invention, instead of or in addition to the above-mentioned amino acid substitution, one or more amino acids are substituted by other amino acids in a region corresponding to a second region consisting of amino acids at positions 278 to 320 in A. C. PQQGDH.

Furthermore, in a further embodiment of the modified PQQGDH, instead of or in addition to the above-mentioned amino acid substitution, in a region corresponding to a third region consisting of amino acids at positions 162 to 197 in A. C. PQQGDH, one or more amino acids are substituted by other amino acids.

Furthermore, in a further embodiment of the modified PQQGDH, instead of or in addition to the above-mentioned amino acid substitution, one or more amino acids selected from the group consisting of amino acids which respectively correspond to amino acids at positions 75, 168 to 347 in A. C. PQQGDH are substituted by other amino acids.

The number of amino acids to be substituted in each region is not particularly limited. However, it is preferable that two or more amino acids are substituted in the case of the region corresponding to the first region.

Furthermore, the position of amino acids to be substituted in each region is not particularly limited. For example, in the region corresponding to the first region, it is preferable that amino acids corresponding to the amino acids at position 342 and/or 351 in the first region are substituted. Similarly, in the region corresponding to the second region, it is preferable that amino acids corresponding to the amino acid at position 295 in the second region is substituted; and in the region corresponding to the third region, it is preferable that amino acids corresponding to the amino acids at position 75 and/or 169 in the third region are substituted.

Herein, the kinds of the amino acids after substitution are not particularly limited. For example, the amino acid at position 75 is tryptophan, the amino acid at position 168 is histidine, the amino acid at position 169 is phenylalanine, the amino acid at position 295 includes glutamic acid, asparatic acid, tyrosine, phenylalanine, etc., the amino acid at position 342 is proline, the amino acid at position 347 is arginine, and the amino acid at position 351 is threonine.

Specific examples of the modified PQQGDH of the present invention include PQQGDH having an amino acid sequence of any of SEQ ID NOs: 28 to 34. Herein, the amino acid sequence of SEQ ID NO: 28 is an amino acid sequence in which amino acids at positions 169, 295, 342 and 351 are substituted by other amino acids respectively in the amino acid sequence (SEQ ID NO: 1) of the wild-type PQQGDH produced by *Acinetobacter calcoaceticus* IFO 12552 strain. Similarly, the amino acid sequence of SEQ ID NO: 29 is an amino acid sequence in which amino acids at positions 295 and 351 are substituted by other amino acids respectively in SEQ ID NO: 1. Similarly, the amino acid sequence of SEQ ID NO: 30 is an amino acid sequence in which amino acids at positions 295, 342 and 351 are substituted by other amino acids respectively in SEQ ID NO: 1. Similarly, the amino acid sequence of SEQ ID NO: 31 is an amino acid sequence in which amino acids at positions 295, 342 and 351 are substituted by other amino acids respectively in SEQ ID NO: 1. Similarly, the amino acid sequence of SEQ ID NO: 32 is an amino acid sequence in which amino acids at positions 169, 295 and 342 are substituted by other amino acids respectively in SEQ ID NO: 1. Similarly, the amino acid sequence of SEQ ID NO: 33 is an amino acid sequence in which amino acids at positions 75, 295, 342 and 351 are substituted by other amino acids respectively in SEQ ID NO: 1. Similarly, the amino acid sequence of SEQ ID NO: 34 is an amino acid sequence in which amino acids at positions 342 and 351 are substituted by other amino acids respectively in SEQ ID NO: 1.

As shown in the below-mentioned Examples, in the modified PQQGDH having an amino acid sequence of SEQ ID NO: 28 or an amino acid sequence of SEQ ID NO: 34, the reactivity with respect to maltose is extremely low. Furthermore, in the modified PQQGDH having an amino acid sequence of SEQ ID NO: 28, an amino acid sequence of SEQ ID NO: 29, an amino acid sequence of SEQ ID NO: 33 or an amino acid sequence of SEQ ID NO: 34, the reactivity with respect to galactose is extremely low.

The modified PQQGDH of the present invention has a feature that the selectivity with respect to glucose is improved as compared with the wild type enzyme. That is to say, the modified PQQGDH of the present invention has a feature that reactivity with respect to maltose or lactose is low and in particular the reactivity with respect to galactose is significantly low as compared with the wild type enzyme. When the reactivity is expressed by relative values respectively relative to 100% (the reactivity with respect to glucose), the reactivity of the modified PQQGDH of the present invention with respect to maltose is preferably 40% or less, more preferably 30% or less and furthermore, preferably 20% or less. Similarly, the reactivity with respect to lactose is preferably 50% or less and more preferably 40% or less. The reactivity with respect to galactose is preferably 20% or less, more preferably 10% or less, furthermore, preferably 5% or less and the most preferably substantially 0%. Note here that just "substrate specificity" herein denotes the selectivity with respect to glucose.

In the modified PQQGDH of the present invention, in addition to the above-mentioned amino acid substation, a part of amino acids may be further modified. The phrase "a part of amino acids is modified" herein is intended to include deletion or substitution of one to several amino acids constituting amino acid sequence, or addition or insertion of one to several amino acids, or the combination thereof so as to change the amino acid sequence. In principle, such modification can be carried out as long as the activity as the PQQGDH (i.e., reactivity with respect to glucose) is maintained. However, even though the activity of PQQGDH is lowered to some degree, in a case where the reactivity with respect to other substrate (for example, maltose or galactose) is also lowered, so that the substrate specificity with respect to glucose is turned out to be improved, or in a case where lowering of the substrate specificity to some degree does not influence on the measurement of an amount of glucose, modification as mentioned above are allowed.

It is preferable that the modification of a part of the amino acids as mentioned above is carried out in a state in which the reactivity with respect to maltose, galactose and the like is kept low.

Herein, the position of the amino acid to be modified is not particularly limited. Furthermore, modification may be carried out in a plurality of positions. "Plurality of positions" herein denotes 10% or less of the number of whole amino acids, and preferably 5% or less. Furthermore preferably, it is 1% or less of the number of whole amino acids.

The modified PQQGDH of the present invention can be also prepared by firstly obtaining gene encoding a wild-type PQQGDH; then modifying the wild-type PQQGDH so as to construct polynucleotide encoding the modified PQQGDH; and finally expressing the polynucleotide in an appropriate expression system. Hereinafter, this preparing method will be described. Note here that once a sequence is designed, based on its sequence information, polynucleotide (gene) encoding the modified PQQGDH of the present invention can be prepared by chemical synthesis using deoxynucleotide triphosphoric acids (dATP, dTTP, dGTP and dCTP).

<Obtaining Gene Encoding Wild-Type PQQGDH>

Firstly, a gene encoding PQQGDH is obtained from bacteria producing PQQGDH. Examples of the bacteria producing PQQGDH include oxidizing bacteria such as *Acinetobacter calcoaceticus*, *Acinetobacter baumannii*, *Pseudomonas aeruginosa*, *Pseudomonas putida*, *Pseudomonas fluorescens*, *Burkholderia cepacia*, *Gluconobacter oxydans*, *Acetobacter aceti*, etc.; and enterobacteria such as *Escherichia coli*, *Klebsiella aerogenes*, etc. Above all, it is preferable that *Acinetobacter calcoaceticus* is used as bacteria producing PQQGDH.

A gene encoding PQQGDH can be extracted from the cell body of the bacteria producing PQQGDH in the usual manner. A PQQGDH gene can also be prepared by employing PCR method, etc. using the genome DNA of PQQGDH as a template. On the other hand, an extracted gene is amplified by using an amplification method such as PCR method, and then the amplification product may be used in the following operations. Note here that after the base sequence of the gene encoding PQQGDH is identified, the targeted PQQGDH gene can be prepared also by a chemical technique. Hereinafter, as one example of preparing a PQQGDH gene, a case where the preparation using *Acinetobacter calcoaceticus* IFO 12552 strain as a starting material will be described in detail.

Firstly, a DNA fragment obtained by isolating and purifying a chromosome of *Acinetobacter calcoaceticus* IFO 12552 and thereafter subjecting it to an ultrasonication treatment, a restriction enzyme treatment, etc. and an expression vector prepared in a linear state are ligated to each other at their both blunt ends or sticky ends so as to be closed with the use of DNA ligase, etc. Thus, a recombinant vector is constructed. A recombinant vector can be also constructed by amplifying the PQQGDH gene by a polymerase chain reaction (PCR) using an oligonucleotide primer designed based on the base sequence of the well-known PQQGDH derived from *Acinetobacter* species L.M.D 79.41 strain and ligating thereof with the use of DNA ligase. Then, the recombinant vector that was constructed by any of the above-mentioned methods is transferred into a host microorganism in which the vector can autonomously replicate. Then, screening is carried out using a marker unique to an expression vector and PQQGDH activity as indices, and thus a host microorganism transformed by a recombinant vector containing a gene encoding PQQGDH is obtained.

After the selected transformant is cultured if necessary, cell body is collected. A recombinant vector is isolated and purified from the collected cell body in the usual manner. Thus, a recombinant vector containing the targeted PQQGDH gene is obtained. The isolation of the PQQGDH gene from the recombinant vector can be carried out by restriction enzyme treatment, etc.

Herein, one example of obtaining PQQGDH gene from *Acinetobacter calcoaceticus* IFO 12552 is described in detail. First of all, a culture medium, which is obtained by culturing *Acinetobacter calcoaceticus* IFO 12552 with stirring for, e.g. 1 to 3 days, is centrifuged so as to collect bacterial cells. Then, the collected cells are dissolved so as to prepare a lysate containing PQQGDH gene. As a method for dissolving bacterial cells, for example, treatment using a lysatic enzyme such as lysozyme can be employed. Furthermore, if necessary, enzymatic treatment with protease, etc. or treatment with a surface active agent such as sodium lauryl sulfate (SDS) may be carried out together. Furthermore, physical crushing method such as freezing and thawing or French press treatment may be combined.

DNA can be isolated and purified in the usual manner from the lysate obtained as mentioned above. For example, it can be carried out by appropriately combining methods such as deproteinization treatment by phenol treatment or protease treatment, ribonuclease treatment, alcohol precipitation, and the like.

In order to obtain PQQGDH gene from DNA isolated and purified from microorganism, a polymerase chain reaction using a primer based on the base sequence of *Acinetobacter* species L.M.D 79.41 strain, which was already specified, is carried out.

Also, the amplification PQQGDH gene can be cloned in an appropriate vector. As a vector to be cloned (cloning vector), a vector constructed as a recombinant vector from a phage or plasmid capable of autonomously replicating in a host microorganism is suitable. Examples of such a phage include Lambda gt 10, Lambda gt11, etc. using *Escherichia coli* as a host organism. Similarly, examples of such a plasmid include pBR322, pUC19, pBluescript, pTrc99A, pGEM-T vector, etc. using *Escherichia coli* as a host organism.

Cloning into a vector can be carried out by inserting PQQGDH gene obtained in the above-mentioned method into a cloning site. Such an operation can be carried out by a well-known method using a restriction enzyme and DNA ligase.

The host microorganism to be used for cloning is not particularly limited as long as a recombinant vector is capable of growing stably and autonomously and expressing an exogenous gene. In general, examples of such host microorganisms include *Escherichia coli* W3110, *Escherichia coli* C600, *Escherichia coli* HB 101, *Escherichia coli* JM109, *Escherichia coli* DH5α, etc.

As a method for transferring a recombinant vector into a host organism, for example, in the case where, for example, the host organism is *Escherichia coli*, a competent cell method using a calcium treatment, electroporation, etc. can be used.

In order to select a host microorganism into which a targeted recombinant vector is introduced appropriately, a microorganism capable of expressing a marker (for example, drug resistant gene) of a vector and capable of expressing GDH activity by the addition of PQQ may be searched. For example, a microorganism which grows in a selective medium based on a drug resistant marker and produces PQQGDH may be selected. The transformant selected in this way can produce a large amount of PQQGDH stably when it is cultured in a nutritional medium.

A base sequence of a wild-type PQQGDH gene obtained by the above-mentioned method is decoded by the dideoxy method described in Science, vol. 214, 1205 (1981) (see FIG. 1, SEQ ID NO: 2). Furthermore, the sequence of amino acids of PQQGDH was estimated by the base sequence determined as mentioned above (see FIG. 1, SEQ ID NO: 1). Note here that gene sequence (SEQ ID NO: 4) and amino acid sequence (SEQ ID NO: 3), which include the signal region, are shown in FIG. 2.

The PQQGDH gene collected from the recombinant vector held by the PQQGDH gene can be easily modified by a genetic engineering technique. Specifically, for example, gene is modified so that amino acid residues in a certain site include substitution, deletion, insertion, addition or inversion.

<Construction of Polynucleotide Encoding Modified PQQGDH>

By adding mutation to PQQGDH gene obtained in this way so that certain amino acids are substituted in an expression product, genes encoding the targeted modified PQQGDH can be prepared. A large number of methods for carrying out the site specific substitution of base sequence are known in this technical field (see, for example, Molecular Cloning, Third Edition, Cold Spring Harbor Laboratory Press, New York) and therefore, an appropriate method can be selected from such methods. Note here that also a random mutation is inserted into PQQGDH so as to produce mutation products, and then the substrate specificities of the expression products of the mutation products (modified PQQGDHs) are compared to each other. Thereby, by selecting genes having a preferable substrate specificity, gene encoding the modified PQQGDH can be prepared. In a case where such a random mutation is inserted, firstly, mutation is inserted into a targeted gene region at random by using, for example, an error-prone PCR, and thus modified PQQGDH gene library is constructed. A multiple substitution containing a combination of useful mutations obtained by random mutation can be obtained by a mutation scrambling method. The mutation scrambling method was reported by Norvartis Pharma in Journal of Bioscience and Industry, vol. 59, No. 3 (2001), P35–38. In this method, the modified enzyme can be evaluated simply and easily by a procedure including culturing the resultant colonies, preparing lysate of bacteria by the use of a lysate enzyme such as lysozyme, and measuring the enzymatic activity.

In order to screen the modified PQQGDH gene library efficiently, a base sequence encoding a histidine tag may be added into a PQQGDH gene in advance. Thus, despite of the change in an amount of production enzyme due to a growing state and expression efficiency, etc., enzyme activity can be evaluated by using a certain amount of enzyme. Specifically, for example, a certain amount of anti-histidine tag monoclonal antibody is adsorbed onto the surface of the substrate such as a microplate having a property of adsorbing protein, a treatment for inhibiting non-specific proteins from being adsorbed thereon is carried out, followed by reacting it with the above-mentioned lysate. Thus, a certain amount of PQQGDH contained in the above-mentioned lysate is made into a solid phase, and the enzyme activity can be evaluated. By carrying out the above-mentioned operation in a 96-well microplate, the enzyme activity of the unit amount of a large number of modified PQQGDHs can be evaluated at one time efficiently.

For example, a clone holding the targeted modified gene is selected as follows. Based on the absorbance at 410 nm one hour after 1-methoxy-PMS and XTT are added into lysate, the activity of PQQGDH is measured. At this time, the sample whose reactivity with respect to maltose is lowered to about 80% or less as compared with the wild-type PQQGDH is firstly selected, and then a clone whose reactivity with respect to glucose is maintained at about 90% or more as compared with the wild-type PQQGDH is selected. Herein, the base sequence of the resultant clone is analyzed so as to confirm the mutation.

<Expression of Modified PQQGDH Gene>

For expression of the modified PQQGDH gene, an expression system using *Escherichia coli* as a host can be used. For example, firstly, the modified PQQGDH gene prepared by the above-mentioned method is inserted into a vector using *Escherichia coli* as a host (for example, a pUC vector, a pBluescript vector) so as to construct an expression vector. The expression vector includes a promoter sequence necessary for expressing the modified PQQGDH in the host, a replication origin, a terminator sequence, and the like.

As a method for introducing (transferring) an expression vector into a host microorganism, a competent cell method using a calcium treatment, electroporation, etc. can be used. Selection of host microorganism into which an expression vector can appropriately introduced can be carried out by using the presence or absence of a drug resistant marker and the presence or absence of expression of the GDH activity when PQQ is added as indices. For example, the microorganism after introducing of an expression vector is cultured in a selection medium capable of growing only in the case where it has drug resistant marker, and then among transformants observed to be grown, a transformant capable of producing a modified PQQGDH may be selected.

By culturing the transformant selected in the above-mentioned operation under conditions where it can be grown and proliferated and the modified PQQGDH gene inserted into an expression vector can be expressed, a large amount of modified PQQGDHs can be produced stably.

As a nutrient of a medium, nutrient that can usually be used for culturing microorganism can be used. As a carbon source, a carbon compound capable of assimilation may be used. For example, glucose, sucrose, lactose, maltose, lactose, syrup, pyruvic acid, and the like can be used. Furthermore, as a nitrogen source, a usable nitrogen compound can be used. For example, peptone, meat extract, yeast extract, casein hydrolysate, soybean cake alkaline extract, and the like, can be used. Besides, salts such as phosphate, carbonate, sulfate, magnesium, calcium, potassium, iron, manganese, zinc, etc., certain amino acids, certain vitamin, and the like, can be used if necessary.

Transformant is cultured under temperature conditions where the transformant can be grown and modified PQQGDH can be produced. For example, the culture temperature can be set at 20° C. to 30° C. The culturing period can be set in consideration of the growing property of the transformant to be cultured, the production property of the modified PQQGDH, or the necessary production amount of the modified PQQGDH and the like. For example, at the time when the yield of the modified PQQGDH reaches maximum, the culture is completed. The culturing period may be about 12 to 72 hours. pH of the medium is adjusted to the range in which the transformant can grow and PQQGDH can be produced. Preferable pH is about 6.0 to 9.0.

The culture medium containing cell bodies producing modified PQQGDH can be used as they are or used after they are subjected to treatment such as concentration treatment or treatment for removing impurities, etc. However, in general, the modified PQQGDH is collected from the culture medium or cell bodies. When the produced modified PQQGDH is a secretion type protein, it can be collected from the culture medium; and the produced modified PQQGDH is other than the secretion type protein, it can be collected from the cell bodies. In case that the modified PQQGDH is collected from the culture medium, for example, culture supernatant is filtrated, subjected to centrifugal treatment so as to remove impurities, followed by carrying out vacuum concentration, membrane concentration, salting out using ammonium sulfate or sodium sulphate, fractional precipitation method by using methanol, ethanol, acetone, or the like, dialysis, heat treatment, isoelectric treatment, various kinds of chromatography such as gel filtration or adsorption chromatography, ion exchange chromatography, affinity chromatography, etc. (for example, gel filtration by using Sephadex gel (Pharmacia Biotech), etc., DEAE sepharose CL-6B (Pharmacia Biotech), octyl sepharose CL-6B (Pharmacia Biotech), CM sepharose CL-6B (Pharmacia Biotech)), and the combination thereof so as to isolate and purify modified PQQGDH product. Thus purified product of the modified PQQGDH can be obtained. On the other hand, when the modified PQQGDH is collected from cell body, by carrying out the filtration and centrifugal treatment, etc. of culture medium, cell bodies are collected, and then the cell bodies are crushed by a mechanical method such as a pressure treatment, an ultrasonic treatment, etc. or by an enzymatic method using lysozyme etc. Thereafter, similar to the above, isolation and purification is carried out so as to obtain a purified product of the modified PQQGDH. Note here that if necessary, by adding a chelating agent such as EDTA and a surface active agent, PQQGDH may be solubilized and PQQGDH can be isolated and collected as an aqueous solution.

It is preferable that the purified enzyme is purified to such an extent that it shows a single band in an electrophoresis (SDS-PAGE).

The purified enzyme obtained as mentioned above can be distributed in a state of particles by, for example, freeze-drying, vacuum drying or spray drying, and the like. At this time, the purified enzyme may be dissolved in a phosphate buffer solution, a TRIS hydrochloric acid buffer solution, or Good's buffer solution in advance. The suitable buffer solution to be used herein is a Good's buffer, and above all, PIPES, MES or MOPS buffer solution is particularly preferable.

The modified PQQGDH of the present invention catalyzes a reaction for producing δ-gluconolactone by oxidizing glucose using PQQ as a coenzyme. Such an enzyme activity can be determined by measuring an amount of PQQ reduced in accordance with oxidization of glucose by PQQGDH by a color reaction with a redox reagent. As the color reagent, for example, PMS-DCIP, 1-methoxy-PMS-XTT, potassium ferricyanide, and the like can be used.

In the present invention, in principle, the PQQGDH activity can be measured by using the following reagent under the following conditions.

<Reagent>
10 mM MOPS (pH 7.0)
1 mM 1-methoxy PMS (phenazine methosulfate)
0.25 mM XTT
5 mM glucose <Measurement Conditions>
140 μl of the above-mentioned reagent mixing solution is preheated at 25° C. for about 5 minutes, followed by adding 0.1 ml of enzyme solution to calmly admix thereof. Thereafter, the admixture is subject to recordation for 15 minutes by a spectrophotometer controlled at 25° C. with water as a control and from the linear part, change in absorbance at 410 nm for 1 minute is measured. In a blind test, instead of enzyme solution, distilled water is added in a test mixture, and change in absorbance of light with 410 nm for 1 minute is similarly measured. In the above-mentioned conditions, the amount of enzyme of ½ μmol of formazan produced per minute is made to be 1 unit (U).

The selectivity with respect to glucose of the modified PQQGDH of the present invention can be evaluated as follows. That is to say, enzyme activities when the substrate are various kinds of sugars such as lactose, maltose, galactose, sucrose and xylose are examined in the similar way to the above. The resultant enzyme activities are expressed as relative values relate to the activity when the substrate is glucose. Thus, the relative activities can be evaluated.

By using the modified PQQGDH of the present invention, it is possible to construct a glucose measurement kit. That is to say, another aspect of the present invention provides a glucose measurement kit containing the modified PQQGDH. In addition to the modified PQQGDH, such a kit can contain a solution such as a buffer solution and a glucose solution as a standard, etc. which are necessary for measurement.

The following examples further illustrate the present invention. These examples are not intended to limit the scope of the present invention.

EXAMPLE 1

Isolation of Chromosomal DNA

Chromosomal DNA of *Acinetobacter calcoaceticus* IFO 12552 strain was isolated by the following method. This strain was cultured in 10 mL of LB medium with shaking at 30° C. over night, and then centrifuged (at 15000 rpm for 10 minutes) so as to collect bacteria. From the collected bacteria, chromosomal DNA was extracted and purified by using a Dneasy tissue kit (QIAGEN K.K.) and dissolved in a TE buffer.

EXAMPLE 2

Preparation of DNA Fragment Containing Gene Encoding PQQGDH, and Construction of Recombinant Vector Containing DNA Fragment The chromosomal DNA obtained in Example 1 was used as a template to amplify a region of DNA including the targeted PQQGDH gene by polymerase chain reaction (PCR) using the following primers. Note here that the primers to be used herein were designed based on a base sequence of soluble PQQGDH (A-M Cleton-Jansen et al., Gen. Genet., 217, 430 (1989)) derived from *Acinetobacter* species L.M.D 79.41 strain.

Forward Primer:
5'-ACAAATCATATAGAGAACTCG-3' (SEQ ID NO: 5)
Reverse Primer:
5'-TTACTTAGCCTTATAGGTGAACTTAAT-GAGAGATCCTGGG-3' (SEQ ID NO: 6)

The PCR was carried out in a solution having the composition shown in Table 1 under conditions of carrying out a reaction at 94° C. for 2 minutes, then 30 cycles of reactions at 94° C. for 30 seconds, at 48° C. for 30 seconds and at 72° C. for 2 minutes, and finally a reaction at 72° C. for 10 minutes.

TABLE 1

| TAKARA LA-taq: | 0.5 μL |
| 10-fold buffer: | 5 μL |
| 25 mM MgCl$_2$: | 5 μL |
| dNTP mix (2.5 mM): | 8 μL |
| Forward primer (10 pmol/μL): | 1 μL |
| Reverse primer (10 pmol/μL): | 1 μL |
| template adjusted to 50 μL by H$_2$O | |

The resultant amplification gene fragment was ligated to a pGEM-T Easy vector (QIAGEN K.K.) and *Escherichia coli* JM109 strain was transformed in this plasmid. Note here that the resultant plasmid was defined as pTGEM-GDHB.

EXAMPLE 3

Determination of Sequence List of Soluble PQQGDH of *Acinetobacter calcoaceticus* IFO 12552 Strain The sequence of the gene fragment inserted into the plasmid pTGEM-GDHB obtained in Example 2 was determined by the use of BigDye Terminator Sequencing Kit (Applied Biosystems Japan Ltd.). The determined base sequence and amino acid sequence are shown in SEQ ID NO: 2 and SEQ ID NO: 1, respectively. Note here that base sequence and amino acid sequence including the signal regions are shown in SEQ ID NO: 4 and SEQ ID NO: 3, respectively. The molecular weight of protein calculated from the amino acid sequence was about 50,000 which was substantially identical with the molecular weight of soluble PQQGDH of *Acinetobacter calcoaceticus*.

EXAMPLE 4

Construction of Expression Vector Containing PQQGDH Gene

The plasmid pTGEM-GHDB obtained in Example 2 was used as a template and polymerase chain reaction (PCR) using the following primers was carried out.

Forward primer: 5'-GCGGCCGCGAATTCAT-GAATAAACATTTATTGGCTA AAATTACTTTAT-3' (SEQ ID NO: 7)
Reverse primer: 5'-GCGGCCGCCTGCAGCTATTACT-TAGCCTTATAGGTG AACTTAATGAGAGATC-CTGGG-3' (SEQ ID NO: 8)

The PCR was carried out in a solution having the composition shown in Table 2 under conditions of carrying out a reaction at 94° C. for 2 minutes, then 30 cycles of reactions at 94° C. for 30 seconds, 55° C. for 30 seconds and 72° C. for 2 minutes, and finally a reaction at 72° C. for 10 minutes.

TABLE 2

| | |
|---|---|
| Sigma KlenTaq: | 0.5 µL |
| 10-fold buffer: | 5 µL |
| dNTP mix (10 mM): | 2.5 µL |
| Forward primer (10 pmol/µL): | 2 µL |
| Reverse primer (10 pmol/µL): | 2 µL |
| template adjusted to 50 µL by H₂O | |

The resultant amplification gene was cut by restriction enzymes EcoRI and PstI. The cut gene fragment was ligated to an expression vector. *Escherichia coli* JM109 strain was transformed with this plasmid. Note here that the resultant expression plasmid was defined as pUK-GDHB(S) (see FIG. 3). When the transformant was cultured in 100 mL of LB medium containing 100 µg/mL of ampicillin and 6 µM PQQ at 30° C. over night, production of PQQGDH was observed. Note here that the molecular weight of this PQQGDH calculated from the amino acid sequence was about 50,000 which was substantially identical to the molecular weight of *Acinetobacter* calcoaceticus IFO 12552.

EXAMPLE 5

Production of *Acinetobacter calcoaceticus* PQQGDH Gene Product 50 mL each of LB medium was dispensed in a 500 mL vol flask and subjected to autoclaving at 121° C. for 20 minutes. After cooling down, to the medium, 100 mg/mL ampicillin solution and isopropyl galactopyranoside (50 µL), which were separately filtrated aseptically, were added and a colony having a PQQGDH expression vector pUK-GDHB(S) was inoculated. Then, the medium was cultured with shaking at 30° C. for 16 hours. When the culture was completed, the PQQGDH activity was about 1 U/mL.

After culturing, the medium was centrifuged so as to collect bacteria. The collected bacteria were suspended in 10 mM Tris-HCL (pH 7.5). Then, the bacteria suspension was ultrasonic disintegrated and then centrifuged again so as to obtain a supernatant as a crude enzyme solution. This crude enzyme solution was treated with a cationic coagulation agent and concentrated by desalting, followed by separating and purifying by a DEAE sepharose (Pharmacia Biotech), CM sepharose (Pharmacia Biotech) column chromatography. Thus, purified enzyme was obtained.

The PQQGDHs obtained by the above-mentioned method showed a substantially a single band in electrophoresis. The specific activity at this time was about 1600 U/mg. Hereinafter, properties of the resultant PQQGDH are described.

Action: D-glucose+artificial electron acceptor
→d-gluconolacton+reduced electron acceptor Thermal stability: 50° C. (pH: 7.0, treatment for 10 minutes)

pH stability: pH 6 to 9 (30° C., treatment for one hour)

Optimum temperature: about 50° C.

Optimum pH: 7.0

Molecular weight: 50,000

EXAMPLE 6

Addition of C-Terminal Histidine Tag of PQQGDH

Firstly, a histidine tag was introduced in the downstream of PQQGDH gene. Then, a PCR was carried out using a primer for adding a stop codon right behind it. A PCR using the following primers was carried out using pUK-GDHB(S) obtained in Example 4 as a template.

Forward primer: 5'-TCACATGTTCTTTCCTGCGT-TATC-3' (SEQ ID NO: 9)

Reverse primer: 5'-ATGGTGATGGTGATGGTGCT-TAGCCTTATAGGTGAA CTTAATGAGA-3' (SEQ ID NO: 10, underline is given to the sequence of 6× histidine tag)

The PCR was carried out under the same conditions as in Example 4.

Then, the PCR using the following primers was carried out in order to introduce a translation stop codon in the downstream of a histidine tag by using an amplified gene as a template.

Forward primer: 5'-TCACATGTTCTTTCCTGCGT-TATC-3' (SEQ ID NO: 9)

Reverse primer: 5'-GCGGCCGCCTGCAGCTAT-TAATGGTGATGGTGCTTA GCCTTA-3' (SEQ ID NO: 11)

The PCR was carried by using the same solution composition and under the same conditions as in Example 4.

The amplified gene obtained by adding a histidine tag and a stop codon in the downstream of PQQGDH was cut with EcoRI and PstI. The cut gene fragment was ligated to an expression vector so as to construct a plasmid. *Escherichia coli*JM109 strain was transformed with this plasmid. Note here that the resultant expression plasmid was defined as pUK-GDHB(S)C-His. When the transformant was cultured in 100 mL of LB medium containing 100 µg/mL of ampicillin and 6 µM PQQ at 30° C. over night, the production of PQQGDH was observed. Note here that the molecular weight of this PQQGDH calculated from the amino acid sequence was about 50,000 which was substantially identical to the molecular weight of *Acinetobacter calcoaceticus* IFO 12552. Furthermore, when general properties were compared with the wild-type PQQGDH obtained in Example 5 as a control, they were found to be equal to each other.

EXAMPLE 7

Construction of Mutant PQQGDH Gene Library

The plasmid PUK-GDHB(S)C-His obtained in Example 6 was used as a template to introduce random mutations by error-prone PCR using the following primers.

Forward primer: 5'-TCACATGTTCTTTCCTGCGT-TATC-3' (SEQ. ID NO: 9)

Reverse primer: 5'-GGCGCGTACTATGGT-TGCTTTGA-3' (SEQ ID NO: 12)

The conditions for introducing mutations are mentioned below. The PCR was carried out in a solution having the composition shown in Table 3 under conditions of carrying out a reaction at 94° C. for 5 minutes, then 25 cycles of reactions at 94° C. for one minute, 50° C. for one minute and 70° C. for 2 minutes, and finally a reaction at 72° C. for 7 minutes.

TABLE 3

| | |
|---|---|
| 100 mM Tris-HCl (pH 8.3): | 0.5 µL |
| 500 mM KCl: | 5 µL |
| 1 mg/mL BSA: | 2.5 µL |
| (15–100 mM) MgCl₂: | 5 µL |
| 1 mM MnCl₂: | 1.25 µL to 3.75 µL |
| 10 mM ATP: | 0.5 µL to 1.55 µL |
| 10 mM TTP: | 0.5 µL to 5.0 µL |
| 10 mM GTP: | 1.0 µL to 5.0 µL |

TABLE 3-continued

| 10 mM CTP: | 0.5 µL to 5.0 µL |
|---|---|
| Forward primer (20 pmol/µL): | 2.5 µL |
| Reverse primer (20 pmol/µL): | 2.5 µL |
| Dimethylsulfoxide: | 0 to 7.5 µL |
| 0.2 ng/µL template: | 5 µL |
| rTaq Polymerase: | 0.5 µL |
| adjusted to 50 µL by H₂O | |

The amplified gene fragment into which the mutation was introduced was cut with EcoRI and PstI so as to be substituted by the wild-type gene of pUK-GDHB(S). *Escherichia coli* JM109 was transformed with the thus obtained plasmid so as to construct a mutant gene library.

The resultant colony was inoculated into 600 µL of Circle Grow Medium (Stratagene) in a 96-well culturing microplate having a deep well. The Circle Grow Medium contained 100 µg/mL ampicillin, 5 µM of PQQ and 1 mM calcium chloride. The medium was cultured with shaking at 200 rpm at 37° C. over night. Thereafter, bacteria were collected through a centrifuge (at 3000 rpm, 4° C., 30 minutes) and suspended in 600 µL of three-times diluted lysate (50 mM TRIS buffer solution, pH 8.0, 2 mM EDTA, 1 mg/mL lysozyme, 15 µM PQQ) again. Then, the suspension was subjected to shaking at 37° C. for one hour and 30 µL of 20 mM calcium chloride solution was added therein. The lysate was transferred to a filter plate (Corning) and centrifuged (at 2000 rpm, at 4° C. for 5 minutes). The resultant supernatant was used for screening mentioned below.

A 96-well microplate to be used for screening was treated in the following method in advance. That is to say, firstly, 100 µL of 15 ng/µL Protein A/G solution was added in a 96-well microplate (Coaster Co., Ltd.) and allowed it stand at 37° C. for about 2 hours, then washed with a PBS solution three times, added by 150 µL of a blocking solution and allowed it stand at 37° C. for about 2 hours. Thus, a microplate for screening was prepared. Into a 96-well microplate containing 80 µL of 0.1 ng/µL mouse IgG1 anti 5× histidine tag monoclonal antibody was prepared in advance, the above-mentioned supernatant was added and admixed, followed by adding into a screening microplate from which 100 µL of blocking solution was washed to be removed with a PBS solution and allowed it stand 25° C. for 1 hour. Thereafter, the microplate was washed with PBS three times and added by 140 µL of PQQGDH assay solution (mixing solution containing 3.5 mL of 4 mM 1-methoxy PMS, 3.5 mL of 1 mM XTT solution, 3.5 mL of 20 mM maltose or glucose solution, 3.5 mL of 40 mM MOPS—NaOH, pH 7.0) and the absorbance at 410 nm was measured at room temperature for 15 minutes.

In the first stage of the screening, a random one-base substitution library was screened with maltose as a substrate so as to identify a clone for expressing a mutant whose enzyme activity was lowered by about 80% or less of that of the wild-type enzyme. The identified mutant strain was screened so as to obtain a clone expressing a mutant whose reactivity with respect to maltose is lower than that with respect to glucose. When the base sequence of these mutant PQQGDH genes was determined, it was clarified that glycine at position 75 was mutated to arginine, glycine at position 295 was mutated to glutamic acid, methionine at position 342 was mutated to valine; alanine at position 351 was mutated to threonine; glutamine at position 168 was mutated to histidine; leucine at position 169 was mutated to glutamine; and tryptophan at position 347 was mutated to arginine. As shown Table 4 below, the modified PQQGDH had lowered specificity to maltose as compared with that of the wild-type. The activity of the wild-type PQQGDH using glucose as a substrate was made 100, and with respect to this, the reactivity with respect to maltose was shown. Note here that as a control, a wild-type PQQGDH added by a histidine tag obtained in Example 6 was used.

In Table 4, numbers in the column of amino acid substitution represent amino acid number and letters written at the left of the numbers are kinds of amino acids in a wild-type and letters at the right of the numbers are kinds of amino acids after being mutated. Therefore, for example, Gly75Arg means a modified product in which glycine that is an amino acid at position 75 was mutated to arginine.

TABLE 4

| Amino acid substitution | glucose | Maltose |
|---|---|---|
| Wild-type | 100 | 97 |
| Gly75Arg | 100 | 72 |
| Gln168His | 100 | 55 |
| Lue169Gln | 100 | 63 |
| Gly295Glu | 100 | 83 |
| Met342Val | 100 | 69 |
| Trp347His | 100 | 85 |
| Ala351Thr | 100 | 59 |

EXAMPLE 8

Introduction of Site-Specific Mutation into Wild-Type PQQGDH Gene and Consideration of Substrate Specificity of Modified PQQGDH A site-specific mutation was introduced into a structural gene of PQQGDH derived from *Acinetobacter calcoaceticus* shown by SEQ ID NO: 4 by using a QuikChange Site-directed Mutagenesis kit (Stratagene). The introduction of mutation was carried out under conditions where a base sequence encoding the amino acids at sites into which the mutation was introduced in Example 7, that is, glycine at position 75, glycine at position 295, methionine at position 342, alanine at position 351, glutamine at position 168, leucine at position 169 and tryptophane at position 347 are substituted so as to encode 20 kinds of amino acids at random. The sequences of primers for substituting the sites by 20 kinds of amino acids are shown in Table 5. Note here that in Table 5, F and R which are given to the end sequence names represent forward and reverse, respectively.

TABLE 5

| Sequence name: | sequence | |
|---|---|---|
| GDHB/G75-F: | 5'-GTAAATGATGCTGATNNNCAAAACGGTTTATTGGG-3' | (35 mer, SEQ ID NO: 13) |
| GDHB/G75-R: | 5'-CCCAATAAACCGTTTTGNNNATCAGCATCATTTAC-3' | (35 mer, SEQ ID NO: 14) |
| GDHB/G295-F: | 5'-CAAATTAAAGATTTANNNCAAAATGGTTTAAAAGTGGC-3' | (38 mer, SEQ ID NO: 15) |

TABLE 5-continued

| Sequence name: | sequence | |
|---|---|---|
| GDHB/G295-R: | 5'-GCCACTTTTAAACCATTTTGNNNTAAATCTTTAATTTG-3' | (38 mer, SEQ ID NO: 16) |
| GDHB/M342-F: | 5'-CCAACCTgTggggATNNNACCTACATTTgCTgg-3' | (33 mer, SEQ ID NO: 17) |
| GDHB/M342-R: | 5'-CCAgCAAATgTAggTNNNATCCCCACAggTTgg-3' | (33 mer, SEQ ID NO: 18) |
| GDHB/A351-F: | 5'-gCCAACggTTNNNCCgTCATCTgCTTATgTCTA-3' | (33 mer, SEQ ID NO: 19) |
| GDHB/A351-R: | 5'-TAgACATAAgCAgATgACggNNNAACCgTTggC-3' | (33 mer, SEQ ID NO: 20) |
| GDHB/Q168-F: | 5'-GATCAGGGGCGTAACNNNCTGGCTTATTTATTC-3' | (33 mer, SEQ ID NO: 21) |
| GDHB/Q168-R: | 5'-GAATAAATAAGCCAGNNNGTTACGCCCCTGATC-3' | (33 mer, SEQ ID NO: 22) |
| GDHB/L169-F: | 5'-GGGGCGTAACCAGNNNGCTTATTTATTCTTACC-3' | (33 mer, SEQ ID NO: 23) |
| GDHB/L169-R: | 5'-GGTAAGAATAAATAAGCNNNCTGGTTACGCCCC-3' | (33 mer, SEQ ID NO: 24) |
| GDHB/W351-F: | 5'-ggATATgACCTACATTTgCNNNCCAACggTTgCgCCg-3' | (37 mer, SEQ ID NO: 25) |
| GDHB/W351-R: | 5'-CggCgCAACCgTTggNNNgCAAATgTAggTCATATCC-3' | (37 mer, SEQ ID NO: 26) |

1 μL of PfuTurbo DNA polymerase (2.5 U/μL) attached to a QuikChange Site-directed Mutagenesis kit, 125 ng of forward and reverse primers, mixture of dNTP, 10 ng of pUK-GDHB(S) and 1/10 amount of a PCR buffer were mixed. The reaction was carried out under conditions for carrying out a reaction at 95° C. for 30 seconds, and then 16 cycles of reactions at 95° C. for 30 seconds, 55° C. for 1 minute and 68° C. for 10 minutes. After the reaction, in order to remove a template DNA, 1 μL of restriction enzyme DpnI (10 U/μL) was added, followed by incubation at 37° C. for one hour. *Escherichia coli* XL1-Blue was transformed by using 1 μL of the reaction product and thus a colony was obtained.

Then, a colony of the resultant transformant was inoculated in 600 μL of Circle Grow medium (Stratagene) and the screening was carried out by the same method as Example 7. As a result, when the base sequence of the selected mutant strain was determined, it was found that various kinds of mutants in which amino acids are substituted as shown in following Table 6. On the other hand, each of these mutants was cultured in 2 mL of LB medium containing 100 μg/mL of ampicillin, 0.01 mM isopropyl thiogalactoside and 6 μM PQQ at 30° C. over night. After being cultured, bacteria were collected by a centrifuge and suspended again in 500 μL of 10 mM MOPS buffer containing 6 μM PQQ (pH 7.0). Then, 250 mg of glass beads (Yasui Kikai Corporation) were added so as to crush the cell bodies by a multibeads shocker (Yasui Kikai Corporation) (crushing operation was carried out 7 cycles of operation for 60 seconds and interval for 30 seconds).

The solution in which cell bodies were crushed was subjected to be centrifuged (15000 rpm, for 10 minutes, at 4° C.) and the supernatant was purified by using His MicroSpin Purification Module (Amersham Pharmacia Biotec). As a result, 200 μL of purified enzyme solution was obtained. Into this purified enzyme solution, PQQ was added to be 5 μM and allowed to stand in the presence of 1 mM calcium chloride for 1 hour or more so as to make it holo.

The substrate specificity of each modified PQQGDH obtained as mentioned above was measured by the following method. That is to say, 50 μL each of the purified enzyme solution was dispersed and 130 μL of assay solution (60 μL of 20 mM solution of 3.3 mM 1-methoxy PMS dissolved in 20 mM MOPS (pH 7.0) and 70 μL of 171 μM XTT) and 20 μL of D-glucose solution was added so that the final concentration became 5 mM. The PQQGDH activity was measured in accordance with the method shown in Example 5. Note here that as a control, a wild-type PQQGDH added by a histidine tag obtained in Example 6 was used. The measurement results are shown in Table 6. As is apparent from Table 6, as compared with the wild-type PQQGDH, any of the modified PQQGDHs have lowered reactivity with respect to both maltose and galactose. Furthermore, at the same time, the modified PQQGDH having lowered reactivity with respect to lactose and galactose was obtained. Note here that in Table 6, numbers in the column of amino acid substitution represent amino acid number and letters written at the left of the numbers are kinds of amino acids in a wild-type and letters at the right of the numbers are kinds of amino acids after being mutated. Therefore, for example, Gly75Arg means a modified product in which glycine that is an amino acid at position 75 was mutated to arginine.

TABLE 6

| Amino acid substitution | glucose | maltose | lactose | Galactose |
|---|---|---|---|---|
| Wild type | 100 | 90 | 75 | 34 |
| Gly75Trp | 100 | 78 | 88 | 42 |
| Gln168Ser | 100 | 35 | 64 | 16 |
| Gln168Gly | 100 | 24 | 63 | 12 |
| Gln168Tyr | 100 | 74 | 69 | 23 |
| Leu169Phe | 100 | 48 | 78 | 33 |
| Gly295Cys | 100 | 80 | 74 | 36 |
| Gly295Asp | 100 | 64 | 77 | 36 |
| Gly295Glu | 100 | 75 | 72 | 37 |
| Gly295Phe | 100 | 75 | 70 | 34 |
| Gly295Val | 100 | 63 | 125 | 37 |
| Gly295Tyr | 100 | 32 | 81 | 28 |
| Met342Pro | 100 | 78 | 61 | 39 |
| Trp347His | 100 | 86 | 90 | 57 |
| Ala351Thr | 100 | 60 | 86 | 21 |

EXAMPLE 9

Introduction of Multiple Mutation Using Mutation Scrambling Method and Consideration of Substrate Specificity of Multiple Substitution A library of multiple-substituted products having any possible combinations of amino acid substitutions effective in improving the substrate specificity which was apparent from Example 8 was prepared by a mutation scrambling method, thereby attempting to obtain a modified product having higher substrate specificity as compared with the case where only one amino acid substitution is contained. The multiple substitution library was prepared by a biased mutation scrambling method which had been already reported was employed (see the 39th Annual Meeting of Biophysical Society of Japan held at Oct. 6, 2001; Subject No: 1PO$_{57}$; Novartis Pharma K. K.; Biopolymer, Vol. 64 (2002), P. 95–105). The biased mutation scrambling method is a modified method of the mutation scrambling method and has a feature capable of freely setting the introduction rate of amino acid substitutions to be combined. In this Example, the rate was set under conditions where G75, G295, M342 and A351 which were located in the vicinity of the substrate binding sites by estimation from a structure model and particularly had high contribution to the substitution specificity included mutations at high rate of 80%; and Q168, L169 and W347 which were thought to have structural features include mutations at the rate of 50%. Specifically, PQQGDH gene was reconstructed by a mutation scrambling method so that the full length of the PQQGDH was divided into 5 fragments shown in FIG. 4 including 1 to 3 amino acid substitutions which were overlapped at the terminal portions and identified in Example 8 were introduced at the above-mentioned rate.

In the mutation scrambling method, firstly, a PCR was carried out using a wild-type gene as a template so as to obtain a partial amplified product (see FIG. 4). The compositions of the reaction solution used in the PCR are shown in Table 7. As the primer, a primer sandwiching G75 and including a sequence corresponding to Q168 and L169 was used.

TABLE 7

| | |
|---|---|
| 10x buffer for AccuTaq (SIGMA CORPORATION): | 2 µL |
| 10 mM dNTP: | 1 µL |
| Forward primer (10 pmol/µL): | 1.2 µL |
| Reverse primer (10 pmol/µL): | 1.2 µL |
| Template (10 ng/µL): | 0.5 µL |
| dH$_2$O: | 13.9 µL |
| AccuTaq (5 units/µL): | 0.2 µL |
| Total: | 20 µL |

Forward primer: 5'-TCACATGTTCTTTCCTGCGTTATC-3' (SEQ ID NO: 9)
S-primer (G)-10-QL: 5'-AAgAATAAATAAgCCAgTTGgT-TACgCCCCTgATC-3' (SEQ ID NO:27)

The reaction was carried out under conditions of 98° C. for 30 seconds, 30 cycles of 94° C. for 5 seconds, 60° C. for 20 seconds, and 68° C. for 90 seconds, and finally 68° C. for 10 minutes. Then, under the same condition, a PCR was carried out by using a modified gene having a mutation at G75 as a template so as to obtain a partial amplified product of the same region as mentioned above. Herein, as shown in Table 6, the number of combinations of the amino acid substitutions at sites G75, Q168 and L169 is 16. The partial amplified products corresponding to all these combinations were prepared by carrying out a reaction using 8 kinds of primers (S-primer(G)-10-QL to S-primer(G)-10-YF) shown in FIG. 4 and using two kinds of genes of wild-type gene and modified type gene as templates. The resultant partial amplified products were mixed at the mixing ratio shown in FIG. 5 so as to obtain a fragment 1 (see fragment 1 in FIG. 4). Fragments 2 to 5 (see fragment 2, fragment 3, fragment 4 and fragment 5 in FIG. 4) were prepared by mixing gene amplified products obtained by using a primer shown in FIG. 4 in the same manner for fragment 1 at the ratio shown in FIG. 5 respectively.

Then, equal amount of each fragment was mixed and a PCR was carried out in a solution having the composition shown in Table 8. The reaction was carried out under conditions of 98° C. for 30 seconds, and 5 cycles of 94° C. for 5 seconds, 60° C. for 20 seconds, and 68° C. for 2 minutes. After the PCR was completed, 2.4 µL each of the above-mentioned primer (10 pmol/µL) (SEQ ID NOs: 7 and 8) was added and a PCR was carried out again. At this time, the reaction was carried out under conditions of 94° C. for 5 seconds, 25 cycles of 60° C. for 20 seconds and 68° C. for 2 minutes, and finally 72° C. for 10 minutes.

TABLE 8

| | |
|---|---|
| mixing fragments: | X µL |
| 10x buffer for AccuTaq (SIGMA CORPORATION): | 2 µL |
| 10mM dNTP: | 1 µL |
| dH$_2$O: | (14.4–X) µL |
| AccuTaq (5 units/µL): | 0.2 µL |
| Total: | 17.6 µL |

The library of the modified gene obtained by the above-mentioned operation was cut by EcoRI and PstI and substituted by a wild-type gene of pUK-GDHB(S), and then transformation of Escherichia coli was performed. Colony of the transformants were cultured in the method shown in Example 8, then screening was carried out with the PQQGDH activity and the substrate specificity as indices. For clones showing the improvement in the substrate specificity, the base sequence of the modified PQQGDH held by the clone was determined. As a result, as shown in Table 6, it was found that a plurality of modified PQQGDHs having different kinds of combinations of amino acids to be substituted. Note here that in Table of FIG. 6, a mark such as G75 (GGA) means that the number specifies the position of an amino acid and one letter of alphabet at the left of the number represents an amino acid at the position. Furthermore, alphabet in parenthesis means the base sequence encoding the amino acid. On the other hand, a mark such as Phe (TTT) shows substituted product in which the mark (for example, L194 (CTG)) that is located at the top part of the column to which the Phe (TTT) belongs is substituted by an amino acid specified by three letters of alphabet. Furthermore, letters in parenthesis means the base sequence encoding the amino acid.

After each transformant having these modified PQQGDH was purified by the same method as in Example 7, the reactivity with respect to substrate was measured. The measurement results are shown in the right column of FIG. 6. As is apparent from this Table, in any of the obtained modified PQQGDHs, the reactivity with respect to maltose was significantly lowered as compared with that of the wild type PQQGDH. Furthermore, as to the reactivity with respect to lactose, the reactivity was found to be lowered similarly. Furthermore, the reactivity with respect to galactose was greatly lowered in any of the modified PQQGDHs, and in some of the modified PQQGDH, the reactivity was extremely lowered. In this way, we successfully obtained modified PQQGDH having the significantly lowered reactivity with respect to maltose, lactose and galactose, that is, having an extremely excellent substrate specificity. As a result, by combining the mutations at the positions of the amino acid shown in Table of FIG. 6, it was found that the modified PQQGDH having more excellent substrate specificity could be prepared as compared with the case where the mutation is a single.

Herein, the amino acid sequence of No. 1 modified product is shown in SEQ ID NO: 28; the amino acid sequence of No. 2 modified product is shown in SEQ ID NO: 29; the amino acid sequence of No. 3 modified product is shown in SEQ ID NO: 30; the amino acid sequence of No. 4 modified product is shown in SEQ ID NO: 31; the amino acid sequence of No. 5 modified product is shown in SEQ ID NO: 32; the amino acid sequence of No. 6 modified product was shown in SEQ ID NO: 33; and the amino acid sequence of No. 7 modified product was shown in SEQ ID NO: 34, respectively.

In particular, in the No. 1 modified product, the reactivity with respect to maltose is lowered to about 1/5 of the wild-type, and similarly the reactivity with respect to lactose is lowered to about 1/2, and the reactivity with respect to galactose is lowered about 1/9, respectively. Furthermore, also in the No. 6 modified product, the reactivity with respect to maltose is lowered to about 1/2 of the wild-type, and at the same time, the reactivity with respect to lactose is also lowered, and the reactivity with respect to galactose is lowered about 1/4, respectively. Similarly, also in the No. 7 modified product, the reactivity with respect to maltose is lowered to about 1/5 of the wild-type, and at the same time, the reactivity with respect to lactose is also lowered to about 1/2. Substantial reactivity is not shown with respect to galactose. From the comparison of the amino acid substitution sites of the No. 1, No. 6 and No. 7 modified products, it is suggested that the substitution of the amino acid at position 342 and the amino acid at position 351 are particularly important for improvement of the substrate specificity. In particular, it is expected that when amino acid are substituted in both positions, high substrate specificity can be obtained. Furthermore, also the substitution of the amino acid at position 295 is also important, and further, the substitution of the amino acid at position 169 is greatly involved in the improvement of the substrate specificity.

The present invention is not limited only to the description of the above embodiments. A variety of modifications which are within the scopes of the following claims and which are achieved easily by a person skilled in the art are included in the present invention.

What is claimed is:

1. A modified pyrroloquinoline quinone-dependent glucose dehydrogenase, comprising a polypeptide in which amino acids corresponding to residues of the following (1) and (2) in pyrroloquinoline quinone-dependent glucose dehydrogenase derived from *Acinetobacter calcoaceticus* are respectively substituted by other amino acids as compared with an amino acid sequence of the corresponding wild-type enzyme:
   (1) an amino acid at position 295; and
   (2) one or more amino acids selected from the group consisting of amino acids at positions 75, 168, 169, 342, 347 and 351.

2. A modified pyrroloquinoline quinone-dependent glucose dehydrogenase, comprising any of the following amino acid sequences (1) to (6):
   (1) a polypeptide in which amino acids corresponding to residues at positions 169, 295, 342 and 351 in pyrroloquinoline quinone-dependent glucose dehydrogenase derived from *Acinetobacter calcoaceticus* are respectively substituted by other amino acids, as compared with an amino acid sequence of the corresponding wild-type enzyme;
   (2) an amino acid sequence in which amino acids corresponding to amino acids at positions 295 and 351 in pyrroloquinoline quinone-dependent glucose dehydrogenase derived from *Acinetobacter calcoaceticus* are respectively substituted by other amino acids, as compared with an amino acid sequence of the corresponding wild-type enzyme;
   (3) an amino acid sequence in which amino acids corresponding to amino acids at positions 295, 342 and 351 in pyrroloquinoline quinone-dependent glucose dehydrogenase derived from *Acinetobacter calcoaceticus* are respectively substituted by other amino acids, as compared with an amino acid sequence of the corresponding wild-type enzyme;
   (4) an amino acid sequence in which amino acids corresponding to amino acids at positions 169, 295 and 342 in pyrroloquinoline quinone-dependent glucose dehydrogenase derived from *Acinetobacter calcoaceticus* are respectively substituted by other amino acids, as compared with an amino acid sequence of the corresponding wild-type enzyme;
   (5) an amino acid sequence in which amino acids corresponding to amino acids at positions 75, 295, 342 and 351 in pyrroloquinoline quinone-dependent glucose dehydrogenase derived from *Acinetobacter calcoaceticus* are respectively substituted by other amino acids, as compared with an amino acid sequence of the corresponding wild-type enzyme; and
   (6) an amino acid sequence in which amino acids corresponding to amino acids at positions 342 and 351 in pyrroloquinoline quinone-dependent glucose dehydrogenase derived from *Acinetobacter calcoaceticus* are respectively substituted by other amino acids, as compared with an amino acid sequence of the corresponding wild-type enzyme.

3. A modified pyrroloquinoline quinone-dependent glucose dehydrogenase, comprising any of the following amino acid sequences (1) to (6):
   (1) an amino acid sequence of SEQ ID NO: 1 in which amino acids at positions 169, 295, 342 and 351 are substituted by other amino acids respectively;
   (2) an amino acid sequence of SEQ ID NO: 1 in which amino acids at positions 295 and 351 are substituted by other amino acids respectively;
   (3) an amino acid sequence of SEQ ID NO: 1 in which amino acids at positions 295, 342, and 351 are substituted by other amino acids respectively;
   (4) an amino acid sequence of SEQ ID NO: 1 in which amino acids at positions 169, 295 and 342 are substituted by other amino acids respectively;
   (5) an amino acid sequence of SEQ ID NO: 1 in which amino acids at positions 75, 295, 342 and 351 are substituted by other amino acids respectively; and
   (6) an amino acid sequence of SEQ ID NO: 1 in which amino acids at positions 342 and 351 are substituted by other amino acids respectively.

4. A modified pyrroloquinoline quinone-dependent glucose dehydrogenase, comprising any of amino acid sequences of SEQ ID NOs: 28 to 34.

5. A modified pyrroloquinoline quinone-dependent glucose dehydrogenase, comprising a polypeptide in which amino acids corresponding to residues at position 295 and one or more amino acids selected from the group consisting of amino acids at positions 75, 169, 342 and 351, wherein at least one amino acid must be an amino acid at position 351, in pyrroloquinoline quinone-dependent glucose dehydrogenase derived from *Acinetobacter calcoaceticus* are substituted by amino acids of the following (i)–(v) as compared with an amino acid sequence of the corresponding PQQGDHs derived from Genus *Acinetobacter*:
   (i) Glu, Asp, Tyr, Phe, Cys or Val substitute an amino acid at position 295;
   (ii) Trp substitutes an amino acid at position 75;
   (iii) Phe substitutes an amino acid at position 169;
   (iv) Pro substitutes an amino acid at position 342;
   (v) Thr substitutes an amino acid at position 351.

* * * * *